(12) United States Patent
Harris et al.

(10) Patent No.: US 8,500,777 B2
(45) Date of Patent: *Aug. 6, 2013

(54) METHODS FOR APPROXIMATION AND FASTENING OF SOFT TISSUE

(75) Inventors: Peter S. Harris, Bellevue, WA (US); Barry Hal Rabin, Idaho Falls, ID (US)

(73) Assignee: Longevity Surgical, Inc., Idaho Falls, ID (US)

( * ) Notice: Subject to any disclaimer, the term of this patent is extended or adjusted under 35 U.S.C. 154(b) by 521 days.

This patent is subject to a terminal disclaimer.

(21) Appl. No.: 12/392,026

(22) Filed: Feb. 24, 2009

(65) Prior Publication Data
US 2009/0318936 A1 Dec. 24, 2009

Related U.S. Application Data

(63) Continuation-in-part of application No. 12/048,206, filed on Mar. 13, 2008, now Pat. No. 8,142,450.

(60) Provisional application No. 61/031,124, filed on Feb. 25, 2008, provisional application No. 60/894,626, filed on Mar. 13, 2007.

(51) Int. Cl.
*A61B 17/08* (2006.01)
*A61D 1/00* (2006.01)

(52) U.S. Cl.
USPC ........................................................ 606/216

(58) Field of Classification Search
USPC ........................................................ 606/219
See application file for complete search history.

(56) References Cited

U.S. PATENT DOCUMENTS

| | | | |
|---|---|---|---|
| 2,808,055 A | 10/1957 | Thayer | |
| 4,165,747 A | 8/1979 | Bermant | |
| 4,724,840 A | 2/1988 | McVay et al. | |
| 5,242,457 A * | 9/1993 | Akopov et al. | 606/144 |
| 5,292,326 A | 3/1994 | Green et al. | |
| 5,332,142 A | 7/1994 | Robinson et al. | |
| 5,345,949 A | 9/1994 | Shlain | |
| 5,355,897 A | 10/1994 | Pietrafitta et al. | |
| 5,389,102 A | 2/1995 | Green et al. | |
| 5,480,406 A | 1/1996 | Nolan et al. | |
| 5,485,952 A | 1/1996 | Fontayne | |
| 5,565,004 A | 10/1996 | Christoudias | |
| 5,643,295 A | 7/1997 | Yoon | |
| 5,662,258 A | 9/1997 | Knodel et al. | |

(Continued)

OTHER PUBLICATIONS

Talebpour, Mohammad, et al., "The Report of Laparoscopic Total Gastric Vertical Plication in Morbid Obesity in Iran," Surgery for Obesity and Related Diseases, vol. 2, Issue 3, p. 332 (May 2006).

(Continued)

*Primary Examiner* — Melanie Tyson
(74) *Attorney, Agent, or Firm* — Ann W. Speckman; Speckman Law Group PLLC

(57) ABSTRACT

Methods for approximating and fastening tissue by application of one or more tissue fasteners are provided. In one embodiment, spaced apart tissue locations are engaged by tissue penetrating members of a deformable fastener, one of more of the engaged tissue locations is moved toward another engaged tissue location to approximate the spaced apart locations, and the deformable fastener is deployed to secure the approximated tissue locations. These methods may be used in laparoscopic plication gastroplasty procedures for forming an invaginated tissue fold, to close holes in the gastrointestinal lumen, and in a variety of interventional procedures.

17 Claims, 29 Drawing Sheets

U.S. PATENT DOCUMENTS

| | | | |
|---|---|---|---|
| 5,700,275 | A | 12/1997 | Bell et al. |
| 5,972,021 | A | 10/1999 | Huttner et al. |
| 6,042,599 | A | 3/2000 | Huttner et al. |
| 6,086,600 | A | 7/2000 | Kortenbach |
| 6,102,922 | A | 8/2000 | Jakobsson et al. |
| 6,273,903 | B1* | 8/2001 | Wilk ................. 606/219 |
| 6,478,791 | B1* | 11/2002 | Carter et al. .............. 606/1 |
| 6,558,400 | B2 | 5/2003 | Deem et al. |
| 6,679,895 | B1 | 1/2004 | Sancoff et al. |
| 6,913,607 | B2 | 7/2005 | Ainsworth et al. |
| 6,986,451 | B1 | 1/2006 | Mastri et al. |
| 7,001,399 | B2 | 2/2006 | Damarati |
| 7,097,650 | B2 | 8/2006 | Weller et al. |
| 7,211,094 | B2 | 5/2007 | Gannoe et al. |
| 7,288,101 | B2 | 10/2007 | Deem et al. |
| 7,556,647 | B2 | 7/2009 | Drews et al. |
| 7,736,372 | B2 | 6/2010 | Reydel et al. |
| 8,100,921 | B2* | 1/2012 | Harris et al. .......... 606/139 |
| 8,142,450 | B2* | 3/2012 | Harris et al. .......... 606/139 |
| 2002/0091395 | A1 | 7/2002 | Gabbay |
| 2002/0165561 | A1 | 11/2002 | Ainsworth et al. |
| 2002/0173803 | A1 | 11/2002 | Ainsworth et al. |
| 2003/0088270 | A1 | 5/2003 | Lubbers et al. |
| 2004/0215216 | A1 | 10/2004 | Gannoe et al. |
| 2004/0225183 | A1 | 11/2004 | Michlitsch et al. |
| 2004/0225305 | A1 | 11/2004 | Ewers et al. |
| 2005/0038449 | A1 | 2/2005 | Sancoff et al. |
| 2005/0080438 | A1 | 4/2005 | Weller et al. |
| 2005/0096673 | A1 | 5/2005 | Stack et al. |
| 2005/0159769 | A1 | 7/2005 | Alverdy |
| 2005/0177176 | A1 | 8/2005 | Gerbi et al. |
| 2005/0192601 | A1 | 9/2005 | Demarais |
| 2005/0216042 | A1 | 9/2005 | Gertner |
| 2005/0228415 | A1 | 10/2005 | Gertner |
| 2005/0234294 | A1 | 10/2005 | Saadat et al. |
| 2005/0234512 | A1 | 10/2005 | Nakao |
| 2005/0247320 | A1 | 11/2005 | Stack et al. |
| 2005/0250980 | A1 | 11/2005 | Swanstrom et al. |
| 2005/0251160 | A1 | 11/2005 | Saadat et al. |
| 2005/0251161 | A1 | 11/2005 | Saadat et al. |
| 2005/0251162 | A1 | 11/2005 | Rothe et al. |
| 2005/0256533 | A1 | 11/2005 | Roth et al. |
| 2005/0267529 | A1 | 12/2005 | Crockett et al. |
| 2006/0020275 | A1 | 1/2006 | Goldfarb et al. |
| 2006/0020276 | A1 | 1/2006 | Saadat et al. |
| 2006/0036267 | A1 | 2/2006 | Saadat et al. |
| 2006/0106288 | A1 | 5/2006 | Roth et al. |
| 2006/0106405 | A1 | 5/2006 | Fann et al. |
| 2006/0135966 | A1* | 6/2006 | Schaller ............... 606/139 |
| 2006/0157067 | A1 | 7/2006 | Saadat et al. |
| 2006/0271076 | A1 | 11/2006 | Weller et al. |
| 2006/0276810 | A1 | 12/2006 | Kelleher et al. |
| 2006/0282118 | A1* | 12/2006 | Surti ................ 606/219 |
| 2006/0293701 | A1 | 12/2006 | Ainsworth et al. |
| 2007/0021760 | A1 | 1/2007 | Kelleher |
| 2007/0043384 | A1 | 2/2007 | Ortiz et al. |
| 2007/0060932 | A1 | 3/2007 | Stack et al. |
| 2007/0112338 | A1 | 5/2007 | Cohen et al. |
| 2007/0112364 | A1 | 5/2007 | Gerbi et al. |
| 2007/0173888 | A1 | 7/2007 | Gertner et al. |
| 2007/0179335 | A1 | 8/2007 | Gertner et al. |
| 2007/0276413 | A1 | 11/2007 | Nobles |
| 2007/0276432 | A1 | 11/2007 | Stack et al. |
| 2008/0249539 | A1 | 10/2008 | Stokes et al. |
| 2008/0249541 | A1 | 10/2008 | Stokes et al. |
| 2008/0249542 | A1 | 10/2008 | Stokes et al. |
| 2008/0249561 | A1 | 10/2008 | Stokes |
| 2009/0024144 | A1 | 1/2009 | Zeiner et al. |
| 2009/0024148 | A1 | 1/2009 | Zeiner et al. |
| 2009/0024163 | A1 | 1/2009 | Zeiner et al. |

OTHER PUBLICATIONS

Fusco, Pedro E.B. MD, et al., "Comparison of Anterior Gastric Wall and Greater Gastric Curvature Invaginations for Weight Loss in Rats," Obesity Surgery, vol. 17, No. 10, pp. 1340-1345 (Feb. 2007).

Fusco, Pedro E.B. MD, et al., "Evaluation of Gastric Greater Curvature Invaginations for Weight Loss in Rats," Obesity Surgery, vol. 16, No. 2, pp. 172-177 (Feb. 2006).

Puccini, Carlos Elias Sales MD, "Surset Gastric Sales: An Alternative for Restrictive Bariatric Surgery," Revista Colombiana de Cirugia, vol. 23, No. 3 (Jul.-Sep. 2008).

Skrekas, George MD, "Laparoscopic Gastric Fold. Without Sleeve Gastrectomy for Obesity," http://www.skrekas.net/surg_faq.htm (Jul. 2008).

Ethicon Endo-Surgery, "Assessment of Gastric Volume reduction in Surgical Weight Loss Candidate," ClinicalTrials.gov, NCT00721227 (Jul. 9, 2008).

Talebpour, Mohammad M.D. et al., "Laparoscopic Total Gastric Vertical Plication in Morbid Obesity," Journal of Laparoendoscopic & Advanced Surgical Techniques, vol. 17, No. 6, pp. 793-798 (2007).

Harris, Peter S.; "Non-Final Office Action," US Patent and Trademark Office, U.S. Appl. No. 12/876,051, filed Sep. 3, 2010, 17 pgs. (Feb. 10, 2011).

Harris, Peter S.; "Non-Final Office Action," US Patent and Trademark Office, U.S. Appl. No. 12/949,725, filed Nov. 18, 2010, 18 pgs. (Mar. 23, 2011).

Harris, Peter S.; "Non-Final Office Action," US Patent and Trademark Office, U.S. Appl. No. 12/184,173, filed Jul. 31, 2008, 11 pgs. (Mar. 15, 2011).

* cited by examiner

METHODS FOR APPROXIMATION AND FASTENING OF SOFT TISSUE

REFERENCE TO PRIORITY APPLICATIONS

This application claims priority to U.S. International Patent Application No. PCT/US2008/56921 filed Mar. 13, 2008 and is a continuation-in-part of U.S. patent application Ser. No. 12/048,206, filed Mar. 13, 2008 and issued as U.S. Pat. No. 8.142.450 on Mar. 27, 2012, which claims priority to U.S. Provisional Patent Application No. 60/894,626 filed Mar. 13, 2007. This application also claims priority under 35 U.S.C. §119(e) to U.S. Provisional Patent Application No. 61/031,124 filed Feb. 25, 2008. These patent applications are incorporated herein by reference in their entireties.

FIELD OF THE INVENTION

The present invention relates generally to methods and devices for approximating and fastening of soft tissues within the body. Uses for the methods and devices of the present invention include laparoscopic and endoscopic interventions involving reconfiguration or repair of soft tissues, such as reconfiguration or repair of gastrointestinal tissues or other soft tissues within the abdominal cavity.

BACKGROUND AND DESCRIPTION OF THE PRIOR ART

The use of devices for tissue approximation and fastening is well known in the art. For example during an open abdominal interventional procedure, an incision is made through the abdominal wall to gain access to the peritoneal cavity. When the surgeon has corrected the abdominal defect, the peritoneum, abdominal muscles, fascial layers and skin must be approximated and fastened to complete the closure of the abdominal cavity. During various interventional procedures a surgical opening created in the stomach must be approximated and fastened closed to allow for the healing process to complete and to prevent stomach contents from entering the peritoneal cavity. In each case the success of the repair and ultimate healing process is highly dependent on the technique and skill of the surgeon. The process of approximating the individual layers of tissue and fastening them securely is tedious and time consuming.

Tissue approximation and fastening is well known throughout history. Suturing materials have been commonly used to aid approximation of tissue for the appropriate duration of the healing process. For example, U.S. Pat. No. 2,808,055 describes a device for surgical stitching that provides an integrated suture dispenser and feeding mechanism to enhance the surgeon's ability to apply sutures quickly and effectively. U.S. Pat. No. 4,165,747 describes methods of both approximating and fastening tissue as it is being held. Further exemplary prior art is disclosed in U.S. Pat. Nos. 5,565,004, 5,643,295 and 5,972,021. The disadvantages and limitations of the methods used in these devices include relatively large skin incisions and resultant scars from providing the surgeon access to the abdominal cavity. Extended time under anesthesia due to the time consuming nature of suturing the wound closed, and lengthy recovery times for patients who undergo these invasive procedures resulting in high costs. These are significant drawbacks for this type of intervention.

Advances in devices for minimally invasive interventions led to combining functionality of approximating and fastening tissues simultaneously. Exemplary prior art is disclosed in U.S. Pat. Nos. 5,332,142, 5,485,952, 5,662,258, 5,700,275 and 6,986,451.

These devices greatly reduced the dependence on the surgeons suturing technique by replacing the suture with surgical staples, furthermore, the mechanically fired staples greatly reduced the time necessary to approximate and fasten tissue thereby shortening the time a patient was kept under anesthesia. Additionally the use of these devices through small incisions in the skin reduced the time required for the patient to recover from surgery. However these devices are complicated to manufacture, expensive and typically require the tissue being fastened must also be transected. Additionally the approximation possible with these types of devices is limited by the size of the aperture of the open jaws of the instrument, often being less than the outside diameter of the instrument shaft itself. Another disadvantage of these devices occurs when the tissue to be fastened does not completely fill the stapler jaws; staples not in contact with tissue fall loosely into the patient's abdomen. These are significant disadvantages for this type of device.

While laparoscopic stapling devices have in many cases improved the speed of interventional procedures and reduced the dependence on an individual's technique to guarantee consistent outcomes, many interventional procedures still require the flexibility offered to the surgeon of needle and thread. Devices like the Autosuture Endo Stitch™ as described in U.S. Pat. No. 5,480,406, provides a device to facilitate suturing laparoscopically. While tedious, time consuming, and technique sensitive, laparoscopic suturing is a method used for fastening tissues to this day. Minimally invasive interventional procedures that use suture in spite of the many disadvantages noted, represent an opportunity for device innovation and improvement when, as in the present invention, these disadvantages can be overcome.

More recently, sophisticated endoscopic devices like U.S. Pat. Application No. 2004/0215216 to Gannoe discloses a tissue approximation and fixation device. The device is used to approximate two folds of soft tissue to form a pleat to be used for gastric reduction surgery or GERD treatment procedures. In this disclosure, the device fixates portions of tissue together so that the tissue can fuse or scar over, however Gannoe specifically discusses the need to apply a clamping force that does not clamp too tightly, thus leading to complications such as pressure necrosis, or too lightly, which may result in an incomplete tissue union. Thus, inconsistent securement is a problem that requires precise application of force. The present invention, as will be shown, provides the appropriate clamping force without the need for precise adjustment of clamping force by the surgeon.

Considering the technical limitations and shortcomings associated with the various methods utilized in prior art to approximate and fasten tissue, as described above, it is apparent that surgeons and patients could benefit from a minimally invasive device that approximates tissues and delivers fasteners in a faster, safer and more consistent manner, thereby providing the surgeon with greater control and flexibility to perform new beneficial interventional procedures.

BRIEF SUMMARY OF THE INVENTION

In general, the devices of the present invention are handheld interventional instruments having a proximal handle assembly, an elongate shaft assembly, and a distal tool assembly. The handle assembly is used to manipulate and position the device, and is further configured with one or more actuation mechanisms that allow the surgeon to control the tissue approximation and fastening functions of the device. The elongate shaft assembly consists of one or more tubular components and provides mechanisms for operatively connecting the actuation mechanisms within the proximal handle assembly to the distal tool assembly. These devices may be configured for use in open, laparoscopic or endoscopic procedures; accordingly, the elongate shaft assembly may be rigid, flexible, articulating, and combinations thereof, and may be rotatable relative to the orientation of the proximal handle assembly.

The distal tool assembly includes mechanisms for engaging tissue at two or more spaced-apart tissue locations on a tissue surface, and is further configured to allow the operator to reposition and/or move at least one of the spaced-apart tissue locations toward another spaced-apart tissue location thereby approximating the engaged tissue locations near the distal end of the device. In certain embodiments, the device may be designed and configured to allow the tissue engagement at two or more locations to be performed sequentially, whereas in other embodiments the device may be designed and configured to the allow tissue engagement at two or more locations to be performed simultaneously. A wide variety of tissue engagement mechanisms are possible within the scope of the present invention, including needles, hooks, barbs, clamps, grippers, forceps, jaws, teeth, vacuum ports, and the like. In certain embodiments, the distal tool assembly further incorporates mechanisms for deploying one or more individual tissue fasteners into the approximated tissue, to securely hold the tissue in the approximated configuration after the device is removed from the treatment site. A wide variety of fasteners may be used within the scope of the present invention, including sutures, staples, screws, tacks, clips, hooks, clamps, rivets, t-tags, expandable anchors, and the like. The devices may be configured to deliver a single fastener, requiring reloading after each tissue engagement, approximation and fastening cycle, or alternatively, in other embodiments, the device may be configured as a multi-fire instrument in which a plurality of fasteners are pre-loaded into the device, allowing successive tissue engagement, approximation and fastening cycles to be completed without reloading or removing the device from the patient. In some embodiments the device is configured having separate and independently operable tissue approximation and fastening mechanisms, whereas in other embodiments multi-functional components provided within the distal tool assembly are designed and configured to provide both the tissue approximation and fastening functions. This can simplify the mechanisms required, lowering cost and increasing reliability, as well as reducing the device profile.

A variety of configurations for the distal tool assembly are possible within the scope of the present invention. For use in minimally invasive laparoscopic and endoscopic procedures, it is generally desirable that the device be provided in an initial collapsed (i.e. pre-deployed) configuration for insertion into the patient, and that after insertion, upon actuation by the user, the device is reconfigured to an expanded (i.e. deployed) configuration. In the deployed configuration, the tissue engagement mechanisms are exposed and positioned appropriately to allow tissue to be contacted and engaged at two or more locations. In certain embodiments, one or more of the tissue engagement mechanisms may be attached to, or fixedly positioned with respect to, the distal end of the device. In other embodiments, separately or in combination with the above, one or more of the tissue engagement mechanisms may also be attached to, or fixedly positioned with respect to, one or more moveable members configured as part of the distal tool assembly. In the latter case, during use the moveable members are capable of being actuatingly controlled by the operator (e.g. remotely, from the handle assembly) such that the tissue engagement mechanism may be repositioned from a location near the distal end of the device to a location away from the distal end of the device in order to engage tissue, after which the motion may be reversed to return the tissue engagement mechanisms, with engaged tissue attached thereto, to a position in proximity to the distal end of the device.

Within the scope of the present invention, movement of the engaged tissue locations toward one another to approximate the tissues can occur by manual repositioning of the distal tool assembly, by actuated movement of one or more moveable members incorporated within the distal tool assembly, and by combinations of the foregoing. After the tissues are approximated near the distal end of the device, one or more fasteners may be deployed from the device to securely hold the tissues in the approximated configuration. In some embodiments, at least a portion of one or more of the tissue engagement mechanisms and/or moveable members are designed to be brought together, joined, mated, or otherwise firmly held in close proximity to one another as an assembly, which is then releasably detached from the device after the tissues have been approximated, being left implanted in the tissue and thereby serving as the tissue fastener to securely hold the tissues in the approximated configuration.

In one embodiment, for example, the distal tool assembly in the deployed configuration provides two or more exposed tissue engagement mechanisms, each of which is fixedly positioned with respect to the distal end of the device, such that in operation, the surgeon first moves the distal end of the device to a first location to engage tissue with a first tissue engagement mechanism, then moves the device to a second location to engage tissue with a second tissue engagement mechanism, dragging the first engaged tissue location to the second, and thereby approximating the engaged tissue locations. In another related embodiment, the two exposed tissue engagement mechanisms are configured as opposite sides of a releasable tissue fastener (e.g. opposing legs of a deformable box-type staple) that is initially at least partially deployed to a first, open configuration, while being firmly held in position near the distal end of the device. After the tissues have been approximated in the manner described, the fastener is actuatingly reconfigured to a second, closed configuration, and then releasably deployed from the device to securely hold the tissue in the approximated configuration.

In another embodiment, for example, there may be a first tissue engagement mechanism positioned fixedly with respect to the position of the distal end of the device, while a second tissue engagement mechanism may be positioned at the distal end of a moveable member that can be repositioned such that its distal end extends away from the device. The moveable member can be rigid, flexible, articulating, and combinations of the foregoing, and the proximal end of said moveable member may be attached to the device using a pivot connection, hinge connection, flexible connection, tether, and the like. In operation, the distal end of the device (having a first tissue engagement mechanism fixedly positioned near its distal end) is used to engage tissue at a first location, while the moveable member (having a second tissue engagement mechanism fixedly positioned near its distal end) engages tissue at a second location. The order in which said engagement is performed is optional and may be determined primarily by convenience. Upon actuated retraction of the moveable member, the second engaged tissue location is drawn in toward the distal end of the device and thereby approximated adjacent the first engaged tissue location that is positioned near the distal end of the device.

In other embodiments, two or more such moveable members are provided, each having an associated tissue engagement mechanism positioned near its distal end. In this example, the step of engaging tissue at two locations occurs after initially deploying the distal end of said moveable members away from the longitudinal axis of the device. Upon actuated retraction of said moveable members, the engaged tissue locations are both moved toward to the longitudinal axis of the device, being moved toward one another and approximated near the distal end of the device. Some advantages of this type of device configuration over the previously described embodiments are that the distal end of the device itself need not become attached to the target tissue, nor does it need to be significantly repositioned to effect the approximation. This results in greater freedom and ease of use for the surgeon, and less variation in the tissue reconfiguration which may be attributable to surgeon technique. As described previously, once the tissues have been approximated near the distal end of the device in this manner, the fastener may be deployed to securely hold tissues in the approximated configuration after the device has been removed from the treatment site.

In another embodiment, one or more tissue engagement mechanisms may be provided at the distal end of one or more moveable members consisting of a releasable flexible tether (e.g. suture, wire, cable, or the like) that is initially retracted and held within the elongate shaft assembly. In this example, the distal end of the device is positioned to engage tissue at a first location, and the flexible tether is released and extended as the distal end of the device is moved freely away, e.g. to engage tissue at a second tissue engagement location. The proximal end of the flexible tether remains connected to the device, much like a dropped anchor remains connected to a ship. In this manner, the flexible tether may later be pulled or retracted back into the shaft of the device, or alternatively a cinching member through which two or more such deployable flexible tethers pass may be slid distally down the length of tethers, thereby pulling on and approximating the engaged tissue locations. Devices of this nature may include tissue engagement mechanisms designed to partially and/or releasably engage the tissue surface (e.g. hooks, clamps, grippers, forceps, jaws, teeth, vacuum ports, and the like), or alternatively, the tissue engagement mechanisms may be designed to fully penetrate through and/or otherwise remain implanted in the tissue (e.g. t-tags, expandable anchors, and the like). These devices may be designed and configured to deploy a single releasable flexible anchor/tether pair, in which case the device must be removed from the patient and reloaded for successive cycles. Alternatively, the device may be configured as a multi-fire instrument having more than one set (i.e. multiple pairs) of releasable flexible anchor/tethers that are pre-loaded into the device and sequentially advanced during operation. In this case, the user can perform a consecutive series of tissue engagement, approximation and fastening steps without reloading or removing the device from the patient.

While the present invention will be described more fully hereinafter with reference to the accompanying drawings, in which particular embodiments are shown and explained, it is to be understood that persons skilled in the art may modify the embodiments herein described while achieving the same methods, functions and results. Accordingly, the descriptions that follow are to be understood as illustrative and exemplary of specific structures, aspects and features within the broad scope of the present invention and not as limiting of such broad scope.

DETAILED DESCRIPTION OF THE INVENTION

Figure 1:
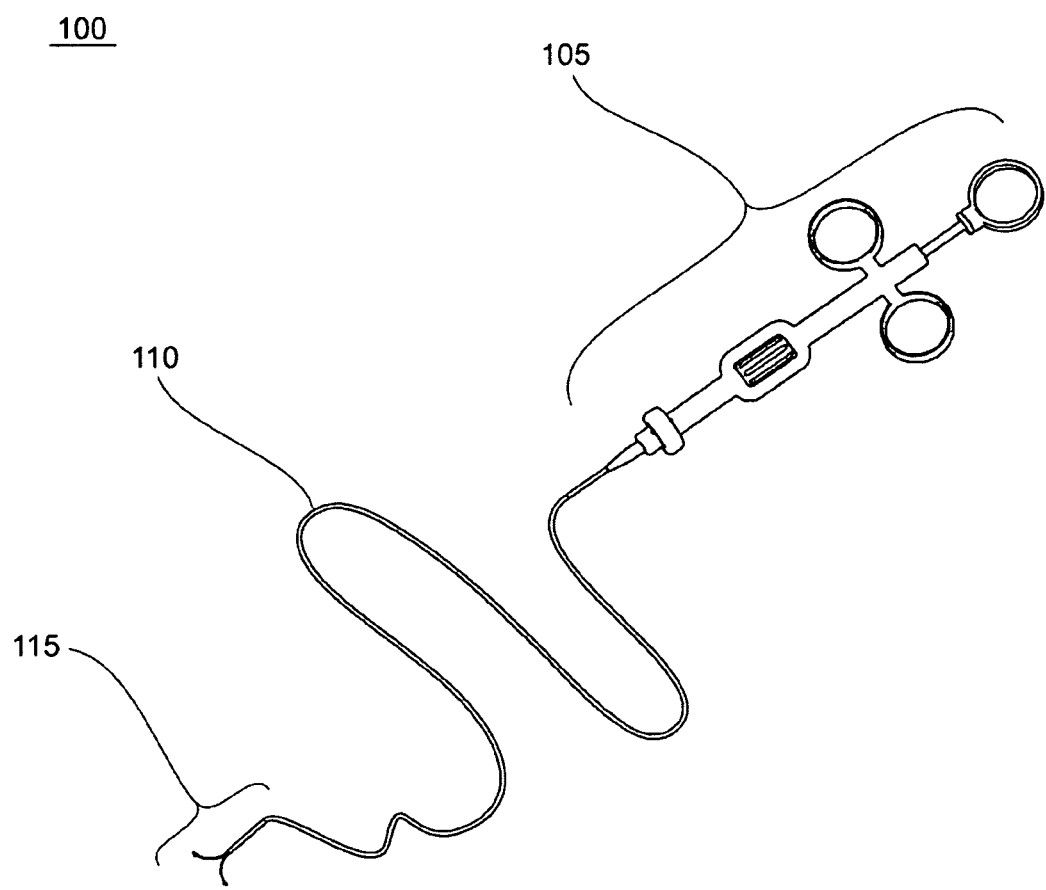
FIG. 1. Overview of a tissue approximation device according to one embodiment of the present invention.

According to one embodiment of the present invention, illustrated in FIG. 1, tissue approximation device 100 is configured for laparoscopic or endoscopic use, consisting of a proximal handle assembly 105, longitudinal tube assembly 110 and distal tool assembly 115. Longitudinal tube assembly 110 is typically produced from flexible biocompatible materials and is configured to be inserted into the body via a laparoscopic access port (e.g. a small incision or trocar) or flexible endoscope. It is preferably between 0.5 mm and 20 mm in diameter, more preferably between 1 mm and 15 mm in diameter, and most preferably between 1.5 mm and 10 mm in diameter. It may consist of a single tube, multiple concentric tubes, and combinations thereof.

Figure 2A:
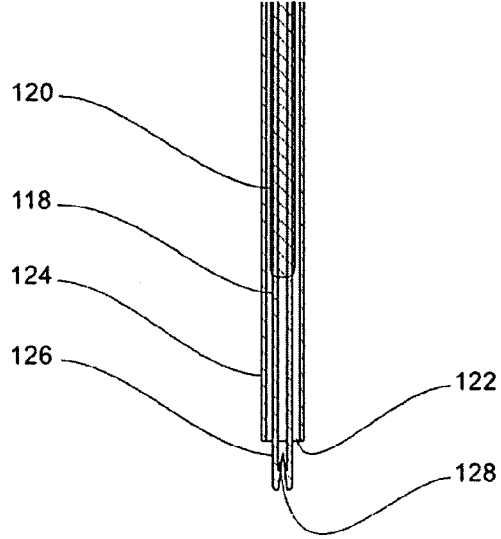
FIG. 2. Close up views of the distal end of a tissue approximation device according to one embodiment of the present invention in the (A) pre-deployed configuration, and (B) deployed configuration.

FIG. 2 shows close up details of distal tool assembly 115. In the pre-deployed configuration (FIG. 2A) two moveable arms 118 are configured as individual longitudinal components that are operatively connected to the distal end of internal shaft 120. Internal shaft 120 is slidably and rotatably positioned within the working channel 122 of outer tube 124, and its motion is actuated from proximal handle assembly 105, as will be described below. As shown in FIG. 2A, in the pre-deployed (i.e. fully retracted) position, moveable arms 118 are held substantially within longitudinal tube assembly 110, with only the distal ends of moveable arms 118 visible near the distal end of device 100.

Each of moveable arms 118 is configured at its distal end with arm tip 126, wherein each said arm tip 126 includes one or more elements whose working function is to controllably, selectively and releasably grasp, grab, grip, pierce, hold or otherwise engage tissue. In the example shown, arm tips 126 incorporate sharp tissue hooks 128. A variety of other configurations and mechanisms are possible within the scope of the present invention for engaging tissue at the distal end of moveable arms 118. For example, teeth, barbs, jaws, graspers, forceps, clamps, vacuum ports, and the like may be used, the choice of which may depend upon the nature of the tissue to be engaged, desired depth of penetration, and so on. In some embodiments, the distal ends of moveable arms 118 (and associated tissue engagement means, such as 126 and sharpened tissue hooks 128) are completely retracted within longitudinal tube assembly 110 in the pre-deployed configuration, such that no portions are exposed that may possibly cause accidental tissue damage during insertion, positioning and/or removal of the device from the body.

Figure 2B:
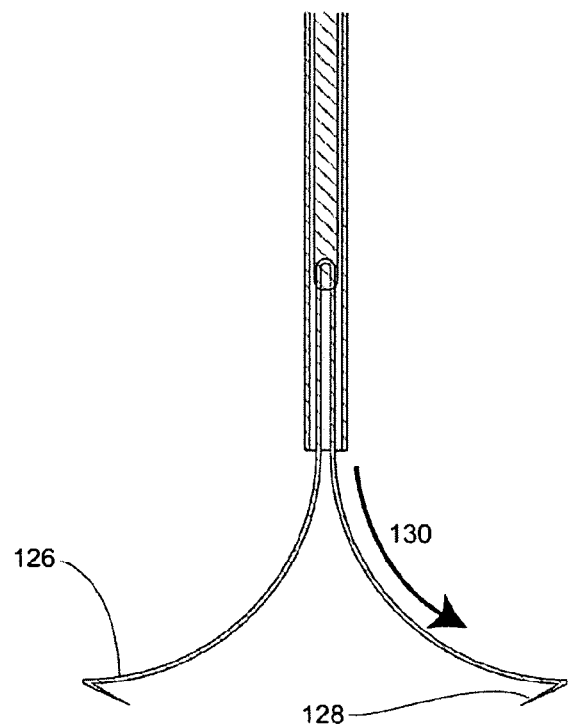

As shown in FIG. 2B, in the deployed configuration moveable arms 118 slide distally 130 and thereby extend out of and away from the distal end of longitudinal tube assembly 110. In this manner, arm tips 126 become spaced apart by a predetermined distance (that may be optionally adjusted by the operator), and the orientation of tissue hooks 128 is altered such that they are placed in a desirable position for subsequently engaging tissue.

Figure 3:
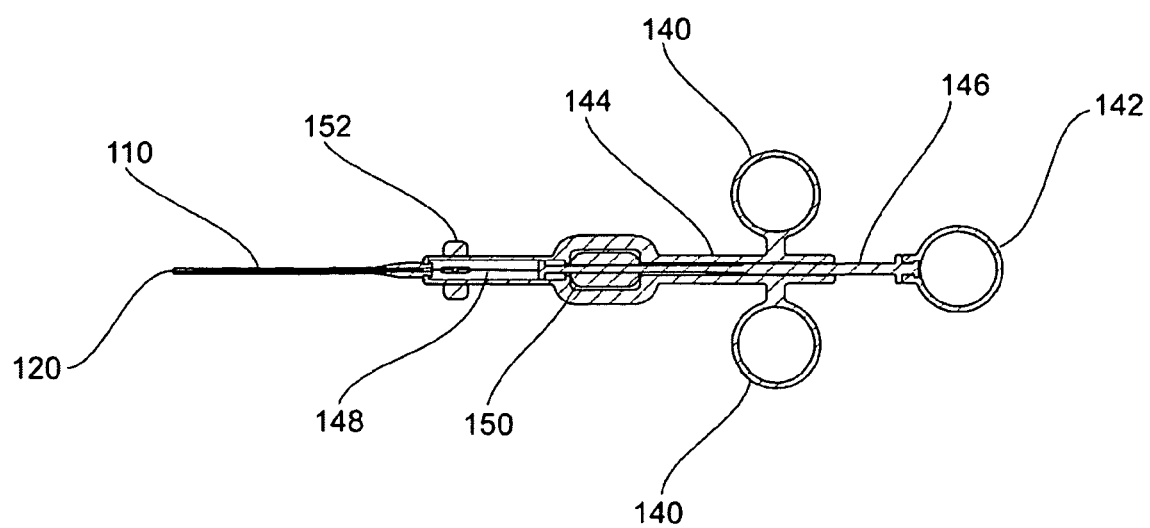
FIG. 3 Close up view of the proximal handle assembly of a tissue approximation device according to one embodiment of the present invention.

FIG. 3 shows a cross section of proximal handle assembly 105. Finger rings 140 and thumb ring 142 are provided to allow the user to grasp the device. Finger rings 140 are fixedly connected to device body 144 whereas thumb ring 142 is fixedly connected to handle shaft 146, which slides proximally and distally within device body 144 when the position of thumb ring 142 is moved relative thereto during actuation by the user. Handle shaft 146 is fixedly connected to internal shaft 120 (described previously) such that actuated distal movement of thumb ring 142 by the user causes distal tool assembly 115 to reconfigure from its pre-deployed to deployed configuration. After tissue has been engaged, as described previously, upon actuated proximal movement of thumb ring 142 by the user causes distal tool assembly to return toward its pre-deployed configuration, thereby approximating the engaged tissue locations near the distal end of device 100.

Also positioned within proximal handle assembly 105 is rotation knob 150 that is fixedly connected to handle shaft 146. Torsion element 148 interconnects handle shaft 146 with internal shaft 120, transmitting the rotational motion of rotation knob 150 thereto, which provides the user an ability to rotatably adjust the orientation of distal tool assembly 115 relative to the position of proximal handle assembly 105.

Figure 4A:
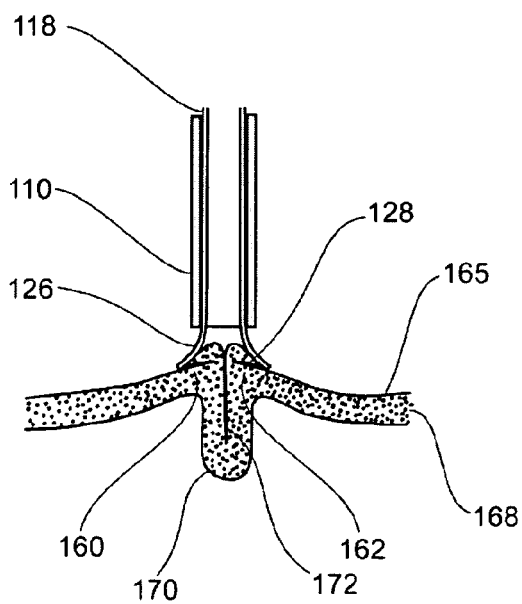
FIG. 4. Close up views of the distal end of an endoscopic tissue approximation device according to one embodiment of the present invention, (A) after deployment, tissue engagement and subsequent retraction to approximate tissue thereby creating a tissue fold, and (B) after deployment, tissue engagement and subsequent retraction to approximate tissue thereby closing a wound or other opening in tissue.
Figure 4B:
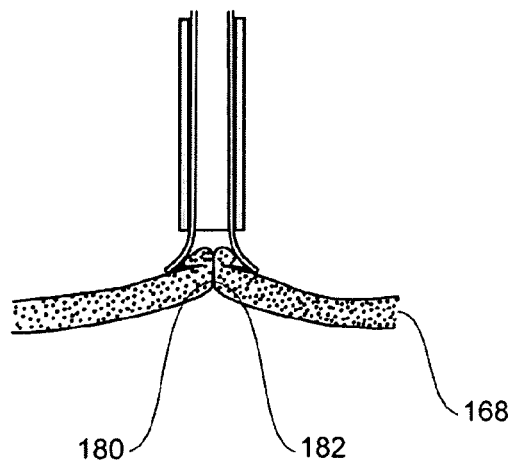

To illustrate the exemplary use of device 100, FIG. 4 shows close up views of the distal end of the device when used to approximate tissue for two different surgical purposes. In both FIG. 4A and FIG. 4B, proximal handle assembly 105 (not shown) of device 100 was previously actuated by the user to deploy moveable arms 118 from within longitudinal tube assembly 110. Tissue was subsequently engaged at two separate and spaced apart locations, 160 and 162, by bringing arm tips 126 having tissue hooks 128 into direct contact with the proximal surface 165 of tissue layer 168. The user then reverse actuated proximal handle assembly 105 to retract moveable arms 118 back toward the original pre-deployed configuration within longitudinal tube assembly 110, which thereby caused engaged tissue locations 160 and 162 to be brought toward one another and approximated substantially near the distal end of device 100. As shown in FIG. 4A, said tissue approximation has been used to create an invaginated tissue fold 170 in tissue layer 168 whose proximal surface 165 positioned within said tissue fold 170 are in intimate contact 172. As shown in FIG. 4B, said tissue approximation has been used to bring together and place in intimate contact opposing edges 180 and 182 of a hole, wound or other type of opening in tissue layer 168.

Figure 5:
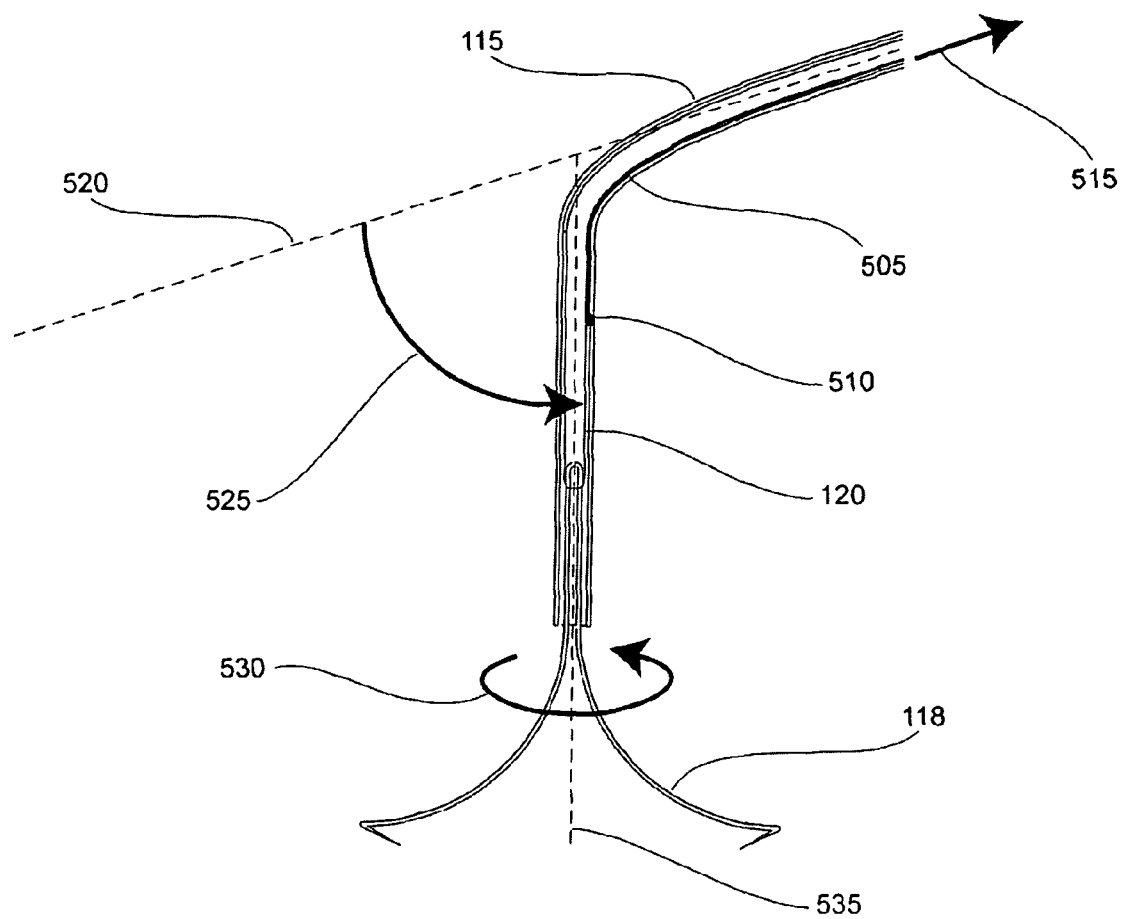
FIG. 5. Close up view of the distal end of an endoscopic tissue approximation device according to one embodiment of the present invention showing articulation and rotation.

FIG. 5 shows a close up view of the distal end of device 100, illustrating means for articulation and rotation of distal tool assembly 115, according to one embodiment of the present invention. Positioned within longitudinal tube assembly 110 is flexible cable 505 that is connected at its proximal end to sliding knob 152 (positioned within proximal handle assembly 105 as shown in FIG. 3) and at its distal end to anchor 510. Anchor 510 is fixedly attached to the interior wall of longitudinal tube assembly 110. When the user actuates sliding knob 152 at proximal handle assembly 105 by moving it in the proximal direction, a tension 515 is applied to flexible cable 505 and transmitted to anchor 515, providing a force component having a direction and magnitude sufficient to cause the distal end of device 100 to bend within the plane established by longitudinal axis 520 and flexible cable 505. The angle of bending 525 is thereby adjustably controlled by the user via the positioning of sliding knob 152 on proximal handle assembly 105. As discussed previously, when the user turns rotation knob 150 at proximal handle assembly 105, a rotational force is transmitted via torsion element 148 to internal shaft 120. This causes rotation of internal shaft 120 within longitudinal tube assembly 110, thereby producing rotation 530 of the plane defined by moveable arms 118 around distal longitudinal axis 535. The angle of rotation 530 is thereby adjustably controlled by the user via the positioning of rotation knob 150 on proximal handle assembly 105.

It is also possible within the scope of the present invention to incorporate into the device more than one flexible cable, as described above. In such cases, by positioning the more than one said flexible cables on opposing and/or orthogonal sides of the longitudinal tube assembly, it is possible to bend the longitudinal tube assembly in more than one direction. Accordingly, the rotational and articulation capabilities that are optionally incorporated into devices of the present invention, as described herein, are important for providing the surgeon the ability to guide, steer, arrange, or otherwise control in three dimensions the position and orientation of the distal portion of the device relative to the target tissue surface in order to place distal tool assembly 115 into the best possible configuration for subsequent approximation and fastening, independent of the handle position or location, orientation, etc., of the body access relative to the target tissue. It should be recognized that other mechanisms known to those skilled in the art may be used to provide such rotational and/or articulation capabilities, and these are considered within the scope of the present invention. For example, pivot joints, flexible joints, hinges, u-connectors, and the like, may be incorporated into longitudinal tube assembly 110 to serve as articulating joints. It should also be noted that it is possible to incorporate more than one articulation mechanism into devices of the present invention in order to further enhance the ability to steer, position and orient distal tool assembly 115, where the number of such articulation joints, there spacing and positioning along the length of longitudinal tube assembly 110, their permitted angle of bending, etc., are all adjustable parameters that may be optimally designed depending on the needs of the mission for a particular interventional procedure. In the case of laparoscopic devices, for example, at least one such articulation joint, along with rotational capability, are desirable to enable tissue approximation and fastening to be performed throughout the entire abdominal cavity from a single point of access, e.g. a single trocar placed through the umbilicus. Such single access port laparoscopic procedures are becoming increasingly desirable for minimizing scarring and healing time for the patient. Alternatively, in the case of endoscopic devices inserted into or through the gastrointestinal tract, a higher degree of control may be desirable, which may require the use of several such articulating joints, whose motions may either be controlled in a coordinated fashion or independently, by using actuating mechanisms incorporated into proximal handle assembly 105 and operably connected to the individual rotational and articulation elements.

The tissue approximating devices of the present invention may further incorporate complementary means for fastening, retaining, holding or otherwise securing tissue in order to substantially maintain the tissue in the approximated configuration. Incorporation of such complementary fastening means typically involves providing within the device one or more suitable tissue retaining fasteners, along with integrated mechanisms for delivering said fasteners to the approximated tissue. Accordingly, the tissue approximating devices, tissue retaining fasteners and integrated fastener delivery mechanisms of the present invention, taken together, comprise systems of the present invention. It should be obvious to those skilled in the art that, within the scope of the present invention, a variety of suitable tissue retaining fasteners and fastener deployment mechanisms that are well known in the art may be incorporated in these systems for the purpose of anchoring, fastening, holding, attaching, or otherwise securing the approximated tissue surfaces. Examples of suitable tissue fasteners that may be used to secure the approximated tissue include but are not limited to sutures, cinches, snares, staples, screws, tacks (e.g. U-shaped, circular and helical fasteners), clips, hooks, rivets, clamps, t-tags, and the like.

Figure 6:
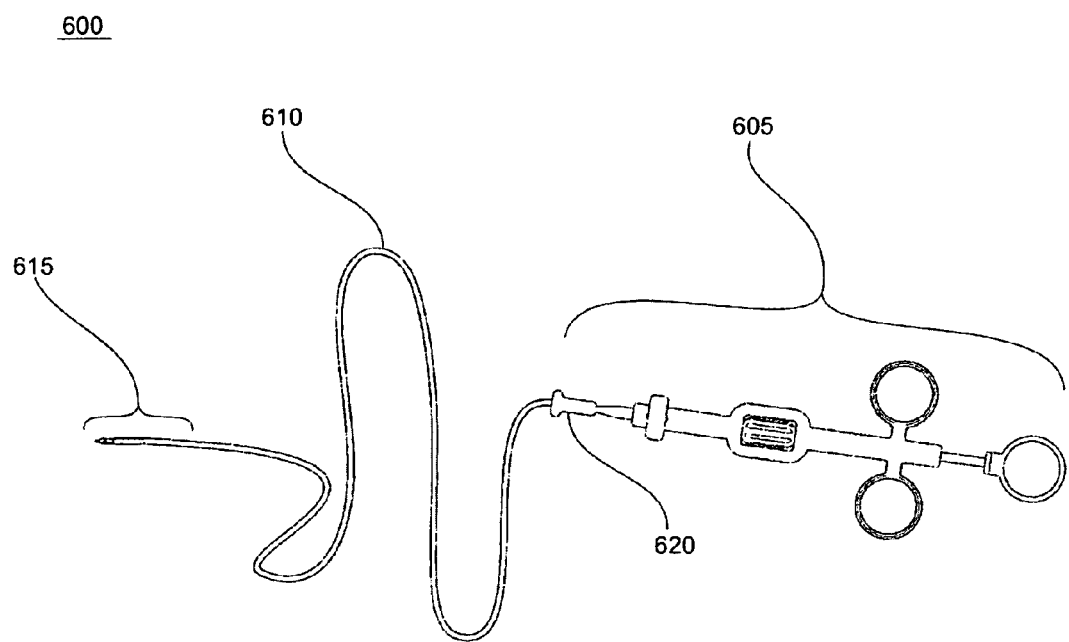
FIG. 6. Overview of a system for tissue approximation and fastening according to another embodiment of the present invention.

One embodiment of the present invention, illustrated in FIG. 6, involves a system 600 configured for flexible endoscopic approximating and fastening of tissue. System 600 includes a tissue approximating device substantially similar to that described above (i.e. device 100). Accordingly, proximal handle assembly 605, longitudinal tube assembly 610 and distal tool assembly 615 are all similar in design and functionality to the previously described embodiment, however, incorporation of the tissue fasteners and integrated fastener delivery mechanisms requires additional components and features. For example, positioned at the intersection between proximal handle assembly 605 and longitudinal tube assembly 610 is fastener deployment knob 620 which can be actuated by the user, after tissue has been approximated, in order to deliver the fastener to the tissue, as explained below.

Figure 7A:
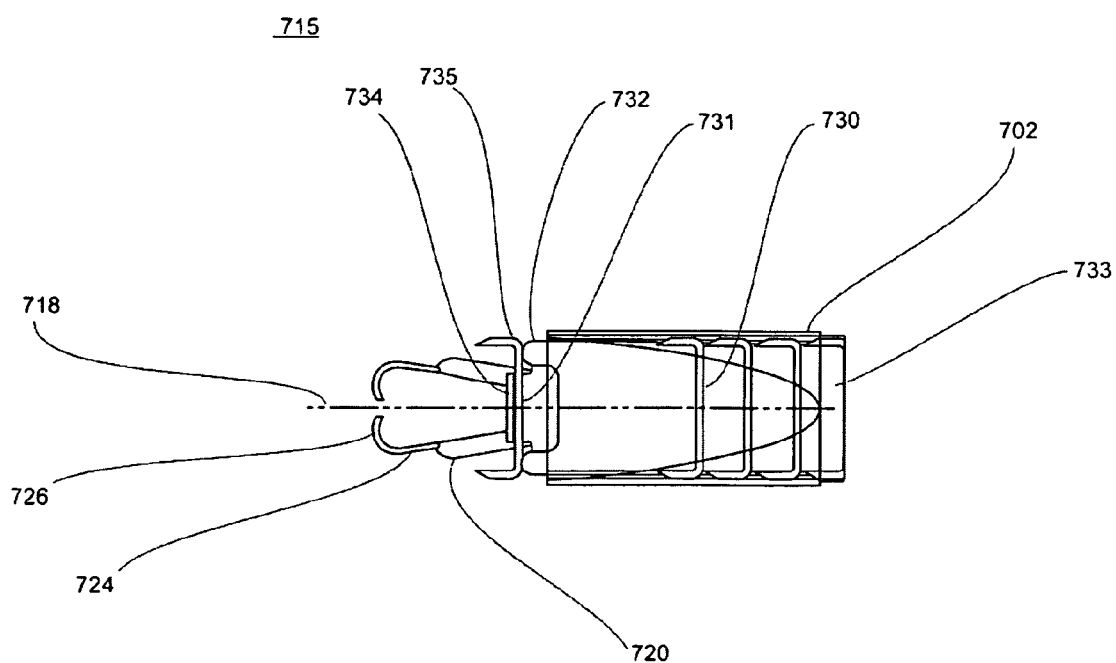
FIG. 7. Close up views of the distal end of an endoscopic system for tissue approximation and fastening according to another embodiment of the present invention (A) pre-deployed, (B) tissue approximated, fastener deployed and device disengaged from tissue.

According to one embodiment of the present invention, the distal tool assembly is configured to approximate tissue and then deliver a box-type staple to secure the tissue in the approximated configuration. FIG. 7A illustrates details of a multi-functional distal tool assembly 715 in the collapsed state. In this configuration, located along longitudinal axis 718 are two (or more) extendible members 720, each being operatively connected to actuating mechanisms accessible to an operator at proximal handle assembly 605. Each of the extendible members 720 is configured at its distal end with a distal tip 724, and each distal tip 724 incorporates one or more tissue engagement mechanisms whose working function is to controllably and selectively grasp, grab, grip, pierce, hold or otherwise engage tissue. In the example shown, distal tips 724 incorporate sharpened tissue hooks 726. Box-type staples in pre-deployed state 730 are stored inside the device and are configured (using, for example, guide channels and a spring loading mechanism well known to those skilled in the art) to slidably move toward the distal end of multi-functional distal tool assembly 715 and into the pre-fire position 731 as staples are sequentially ejected from the device. Pistons 732 are positioned at the distal end of staple forming shaft 733, and, along with stationary anvil 734, are used to deform the legs 735 of staple 731 and thereby reconfigure and eject the staples when the device is actuated by the user. Typically the entire staple forming assembly is protected from contacting tissue during device insertion and removal by being positioned inside longitudinal tube assembly 610, with only the distal portions anvil 734 and staple legs 735 exposed prior to deploying the fastener. Alternatively, it may be desirable to configure the staple forming assembly to be partially exposed by extending it distally beyond the end of longitudinal tube assembly 610, or to retract a distal portion of longitudinal tube assembly 610, during actuation. Although linearly slidable pistons 732 are shown in this embodiment, it should be recognized that other mechanical mechanisms known to those skilled in the art may be used to transmit the actuating mechanical forces to staple legs 735 to thereby deform and deploy the fastener, for example, cams, levers, gears, and the like may be used.

Figure 7B:
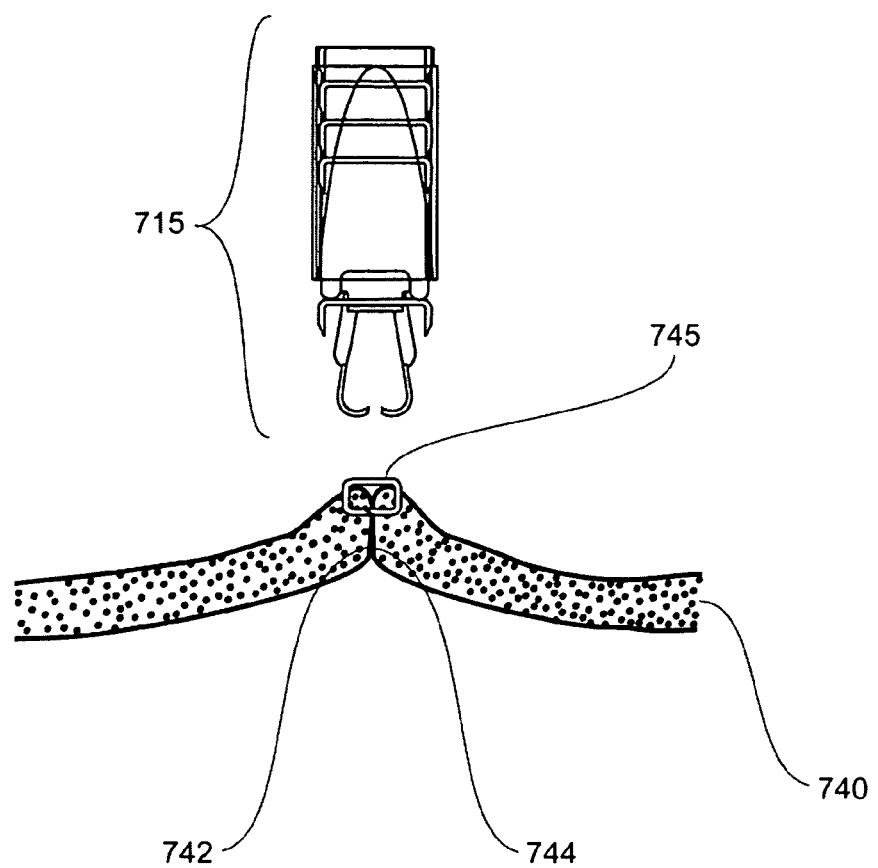

FIG. 7B shows a deformed staple after ejection, implanted in and securely fastening the approximated tissue. In this example, similar to situation described in FIG. 4B, the device is used to close a hole-type defect present in tissue layer 740 by engaging and approximating tissue on opposing sides of the hole, for example at locations 742 and 744, and then deploying fastener 745 to securely maintain the tissue in the approximated configuration. To accomplish closure of the hole-type defect in tissue as shown in this example, distal tool assembly 715 was first positioned within proximity of the defect, and the device was then actuated by the user to deploy the extendable members. The tissue on opposing sides of the opening were engaged by the tissue engagement mechanisms (sharpened tissue hooks in this example), and then the device was actuatingly retracted by the user to pull the engaged tissue locations toward the central axis of the device, thereby approximating the tissue near the distal end of the device. The user then actuated the fastener deployment mechanism to deform and eject the box-type staple, as described previously.

Figure 8A:
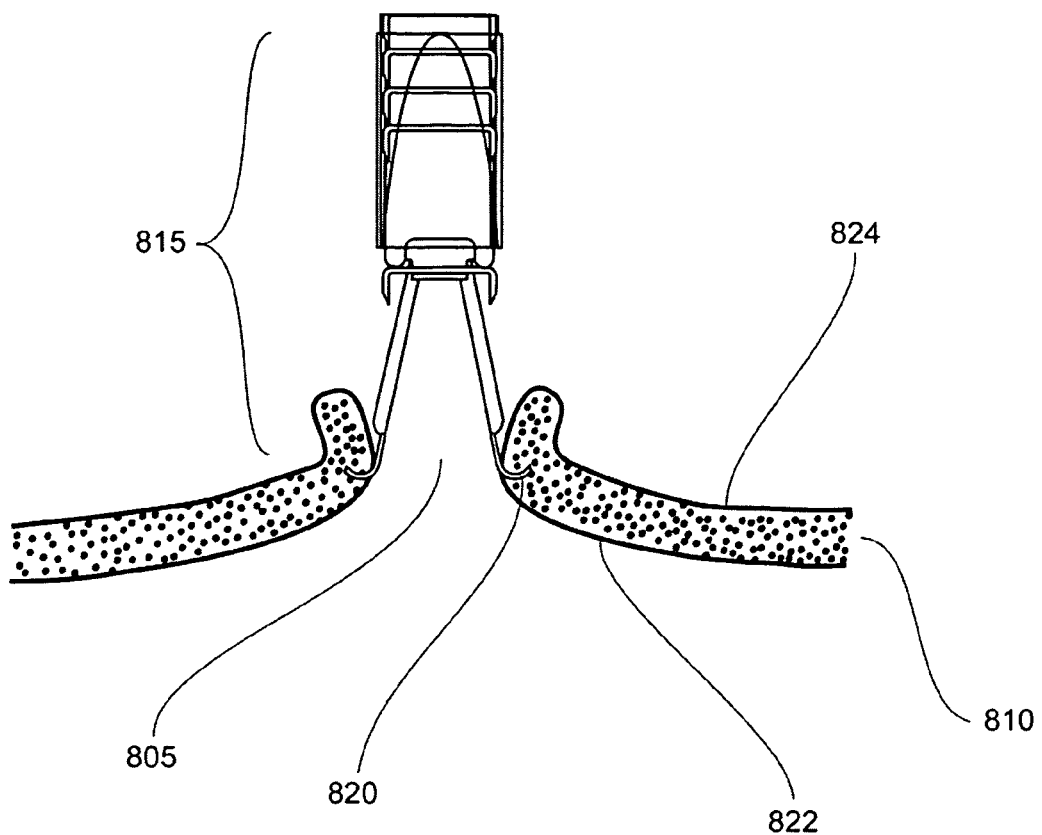
FIG. 8. Close up views of the distal end of a tissue approximation and fastening device according to another embodiment of the present invention, (A) device inserted through hole in tissue, with moveable members deployed and tissue hooks positioned to engage the distal tissue surface, (B) tissue approximated, fastener deployed and device disengaged from tissue.
Figure 8B:
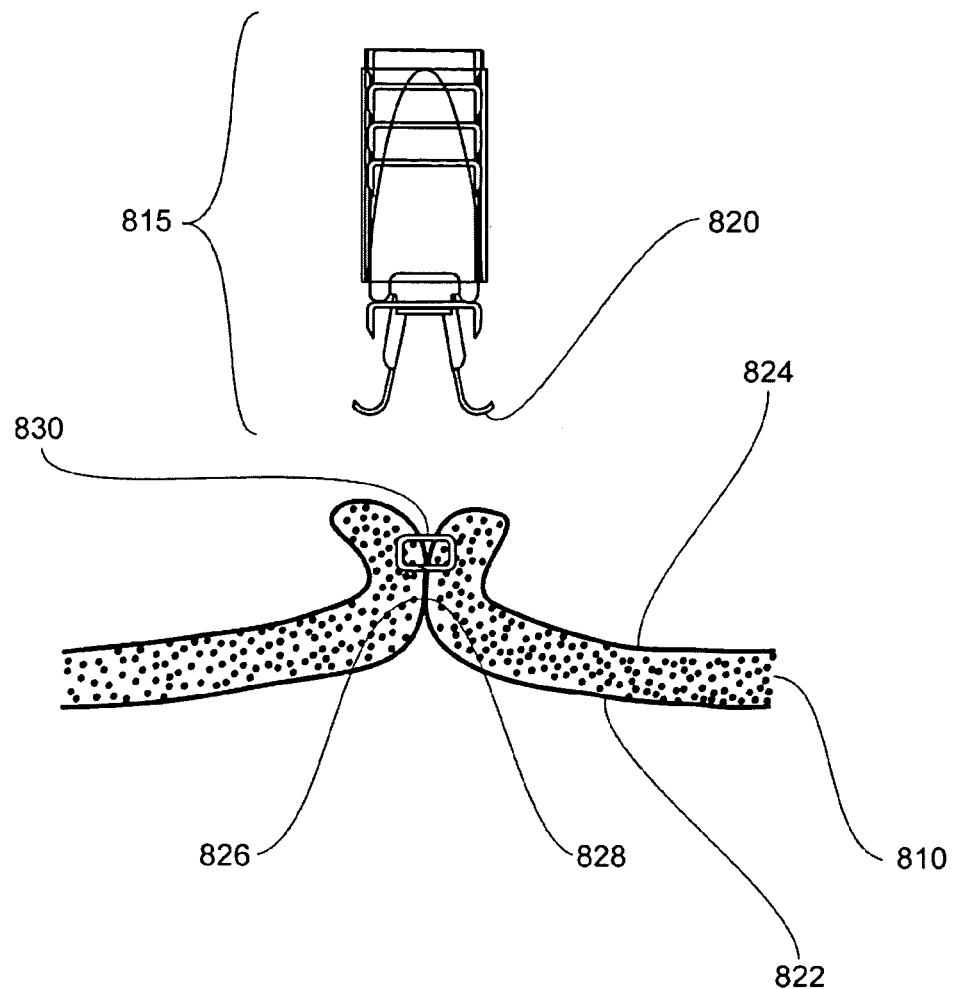

In other embodiments of the present invention, it may be advantageous to employ various other alternative configurations for the tissue engagement mechanisms, depending on the nature of the tissue to be engaged and purpose of the interventional procedure. For example, as shown in FIG. 8, in the case where there is a hole-type defect 805 present in a gastrointestinal tissue layer 810, and it is desired to safely close and more permanently repair said hole-type defect using an entirely endoscopic approach (i.e. from inside the gastrointestinal lumen), it may be desirable to reverse the direction of the sharpened tissue hooks. Such a configuration is illustrated in FIG. 8A, where distal tool assembly 815 incorporates sharpened tissue hooks 820 that are oriented pointing away from the central axis of the device. As shown, this allows the user to position the device directly over hole-type defect 805, and the extendable members can therefore be deployed inside hole-type defect 805, either partially or completely penetrating through gastrointestinal tissue layer 810. In this manner, sharpened tissue hooks 820 are able to engage tissue located on the opposite (i.e. outside the gastrointestinal lumen) tissue surface. The outside surface of gastrointestinal tissue layer is covered by serosal tissue layer 822 that is thin, yet extremely tough, and therefore provides for a much stronger and more secure fastener placement compared to deploying the fastener into the interior mucosal tissue surface 824. The serosal tissue layer is also known to heal itself rapidly and it will form a strong bond to itself within 14 days after the intervention, resulting in a defect-repair that is more durable and permanent that that provided by a fastener alone. As shown in FIG. 8B, the use of outward facing sharpened tissue hooks 820 allows the serosal tissue surfaces on opposing sides of the hole-type defect, as shown at 826 and 828, respectively, to be brought into intimate contact when the tissue is approximated by the actuated retraction of the extendable members. The subsequent deployment of box-type staple 830 into the issue then provides secure fastening of the intimate serosa-to-serosa contact that is established during tissue approximation.

In embodiments where the device is designed to engage tissue on the opposite side of the target tissue layer from the direction of approach by the device, as in the situation described above with regard to FIG. 8, other necessary modifications may be incorporated to allow the approximated tissue to be readily and controllably released from the distal end of the device, without interference, after the fastener has been placed. For example, it may be desirable that, prior to fastener deployment, the approximated tissue first be pulled along the length of, or into, the longitudinal tube assembly, proximally to a position beyond the position where the fastener deployment occurs. This configuration allows the tissue engagement mechanisms to release the tissue upon slight distal actuation of the moveable arms after fastener deployment. In another embodiment, the sharpened tissue hooks may be produced from a highly elastic, flexible material, such as spring steel, superelastic alloy (e.g. NiTi) or the like. In this case, the tissue hooks may be designed having an elastic strength limit such that during the initial actuated retraction of the moveable arms, the hooks are strong enough to retain their shape, remaining in the configuration suitable for tissue engagement and approximation, but after the fastener is deployed, the user can actuatingly increase the proximal tension on the moveable arms to a value sufficient to elastically deform the tissue hooks, which then at least partially straighten and pull out of the tissue to release the engagement, followed by recovery of their shape to the proper tissue engagement configuration when the tension is removed. In yet another embodiment, the distal tool assembly may be configured having one or more vacuum ports in communication with a remote vacuum source, such that after tissue approximation, the vacuum can applied and used to hold the engaged tissue locations in the approximated configuration, while the tissue hooks are released from the tissue and repositioned out of the way, so as not to interfere with subsequent fastener deployment. After the fastener is deployed to securely maintain the tissue in the approximated configuration, the vacuum can be removed and the tissue released from the distal end of the device.

According to another embodiment of the present invention, FIG. 9 shows close up details of the distal end of system 900, along with a target tissue layer 950 having a hole-type defect 960 therein, in order to illustrate the operational sequence of the device, as well as details of the fastener design and delivery mechanism. In FIG. 9A, the device is shown in the pre-deployed configuration prior to contacting tissue, i.e. moveable arms 918 are retracted into longitudinal tube assembly 910. Fasteners 902 to be deployed into tissue are positioned near the distal end of the device. In this example, fasteners 902 are crown-shaped, i.e. they have a cylindrical base 904 and two or more circumferentially arranged legs 906 that extend distally, with sharpened tips 908 designed for penetrating tissue. Fasteners 902 are pre-loaded onto, and designed to slide along, guide shaft 912, forming a magazine within longitudinal tube assembly 910. When positioned near the distal end of the device, fasteners 902 may optionally be covered by an outer tube (not shown) in order to protect the trocar seal during device insertion and to prevent accidental damage to tissue. During post-firing retraction of one fastener, the fasteners within the magazine are advanced distally, one-by-one, into the pre-fired position, by a spring-loaded mechanism (not shown) positioned inside longitudinal tube assembly 910, toward the proximal end of the fastener magazine. Fasteners 902 may be rigid, deformable and combinations thereof. In one embodiment, fasteners 902 are produced from highly elastic material (e.g. spring steel, superelastic alloy such as NiTi, or the like) and are designed to reconfigure in a self actuating manner from a first configuration (e.g. the loaded and pre-fired configuration, as shown) to a second configuration when deployed (e.g. having legs that at least partially change shape to close, grab, grasp, or otherwise more effectively engage the target tissue). Optionally, the legs 906 and/or sharpened tips 908 of fasteners 902 are further configured with at least one or more features positioned on their tissue contacting surfaces that are designed to prevent the fasteners from slipping, migrating, coming out or otherwise moving after being deployed into tissue. Examples of such features, well known in the art, include barbs, teeth, serrations, and hooks, among others.

Figure 9A:
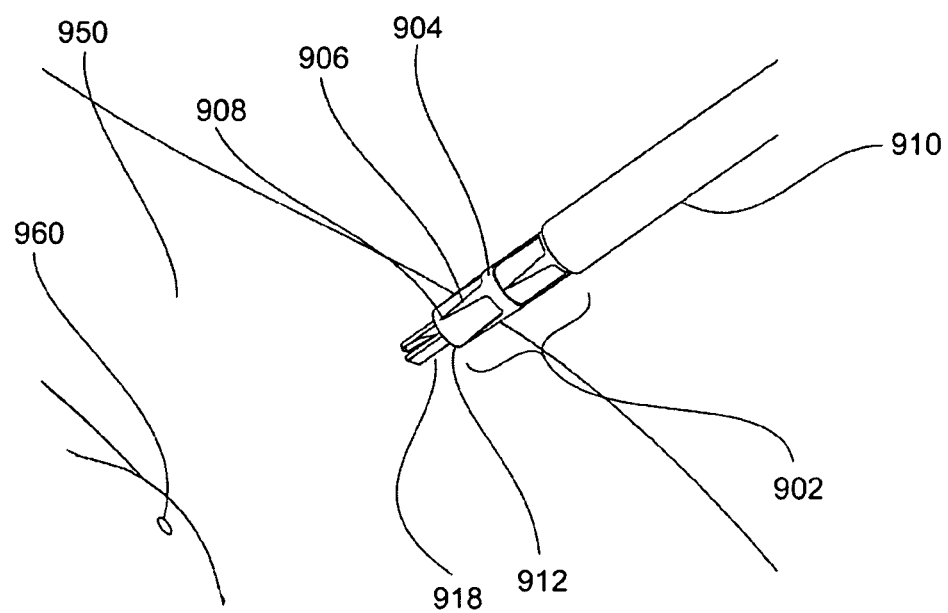
FIG. 9. Close up views of the distal end of an endoscopic system for tissue approximation and fastening according to another embodiment of the present invention (A) pre-deployed, (B) moveable arms deployed, (C) tissue approximated and fastener being deployed, and (D) fastener deployed and device removed.
Figure 9B:
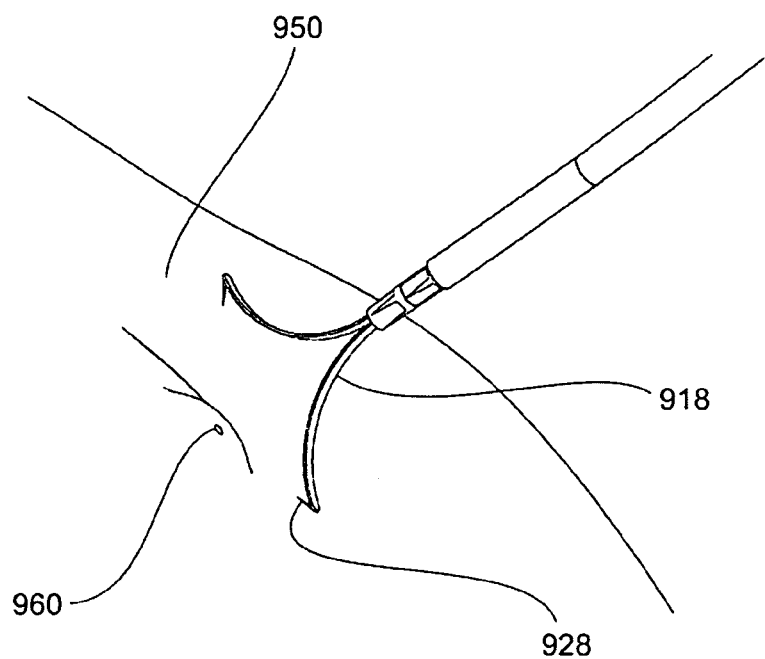
Figure 9C:
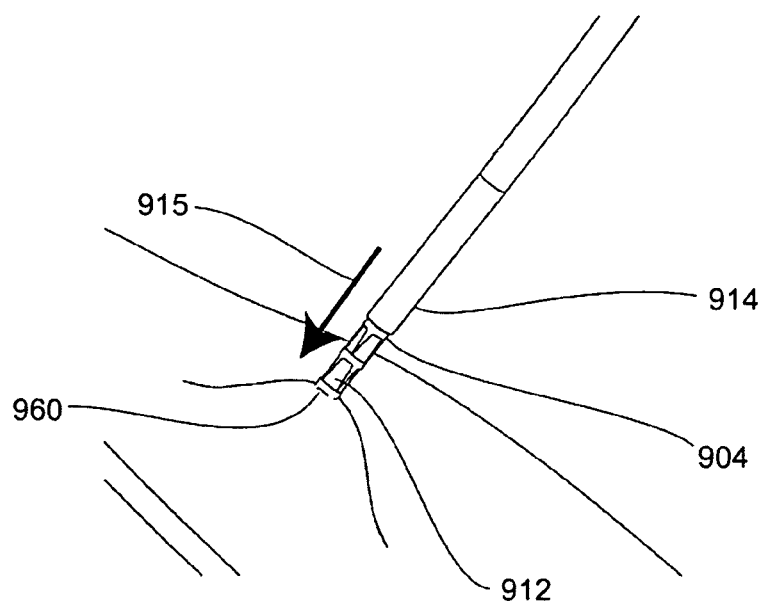
Figure 9D:
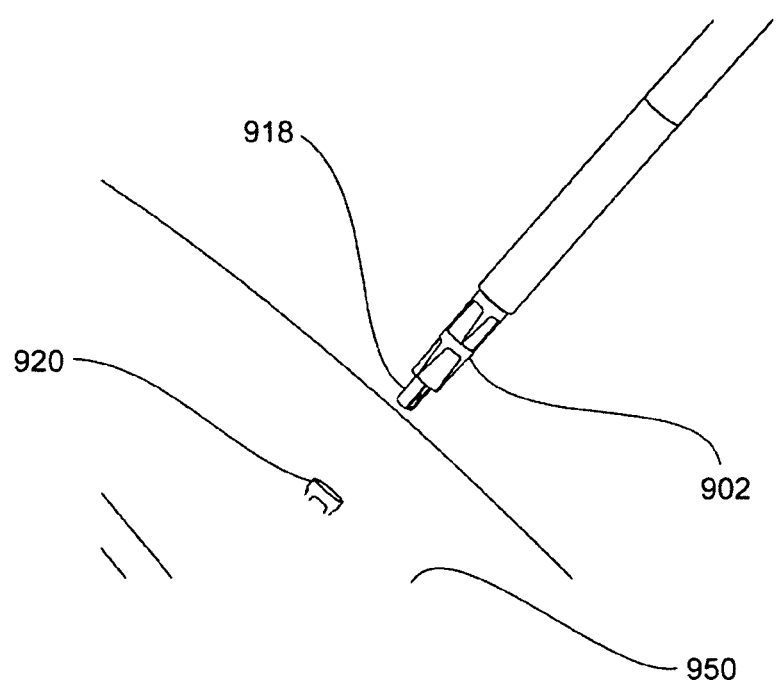

In FIG. 9B, the proximal handle assembly (not shown) has previously been actuated by the user, thereby causing moveable arms 918 to move to the deployed configuration, extending out of and away from the distal end of the device, and being positioned appropriately with tissue hooks 928 located over top of defect 960 in tissue layer 950 in order to subsequently engage tissue. In FIG. 9C, the tissue has been engaged on opposite sides of the defect 960, and the user has reverse actuated proximal handle assembly (not shown) in order to retract moveable arms 918, thereby causing the engaged tissue locations to move toward one another and the tissue to be approximated near the distal end of the device. Fastener deployment tube 914 is configured as a movable outer portion of longitudinal tube assembly 910 that is designed to slide over guide shaft 912 and push against the proximal edge of crown 904 on fastener 902 when the fastener deployment knob (located at proximal handle assembly, not shown) is actuated by the user by pushing distally. As shown in FIG. 9C, this provides a distally directed longitudinal force 915 that pushes fastener 902 off the end of guide shaft 912, thereby penetrating the tissue. As shown in FIG. 9D, after disengaging from the tissue, moveable arms 918 are retracted back to the pre-deployed configuration, and a deployed fastener 920 is implanted in the tissue 950 and thereby securely holds the tissue in the approximated configuration. As further shown in FIG. 9D, the next pre-loaded fastener 902 is automatically moved into the pre-fired configuration, ready for deployment as the above procedure may be optionally repeated.

Alternative novel embodiments for systems that incorporate a fastener and fastener delivery mechanism into the tissue approximation devices of the present invention will now be described. In these embodiments, the tissue approximation device is configured such that at least a portion of at least one of the moveable members, typically a portion involving at least the arm tip having associated tissue engagement means, break offs, disengages or is otherwise actuatingly and controllably released to remain behind, engaged with and implanted within the target tissue that has been approximated, thereby acting as the securing means. This "break-away" fastener concept greatly simplifies the overall device construction, especially for use in circumstances when only a single fastener may be needed, or when manual fastener reloading is acceptable, for example in the hole-type defect closure application. This allows for a smaller device footprint, eliminating the need for incorporating separate individual pre-loaded fasteners and associated multi-fire fastener delivery mechanisms within the device. It also completely avoids any difficulties associated with releasing the engaged tissue from the distal end of the device after fastener placement, obviating the needs for special design considerations when engaging tissue on the opposite side of the target tissue layer from the direction by which the device approaches.

According to one embodiment of the present invention, FIG. 10 shows close up details of the distal end of a tissue approximation and fastening system 1000, along with a target tissue layer 1050 having a hole-type defect 1060 therein. In FIG. 10A, the device is shown in the pre-deployed configuration prior to contacting tissue, i.e. the moveable arms 1005 are retracted into longitudinal tube assembly 1010. Note in this example that tissue hooks 1015 are configured to face outward rather than inward in order to allow the tissue surface on the opposite side from which the device approaches to be engaged, as described shown previously (i.e. in FIG. 8). Positioned and releaseably held in place at the distal end of longitudinal tube assembly 1010 is retainer ring 1020, through which moveable arms 1005 slidably pass when actuated.

Figure 10A:
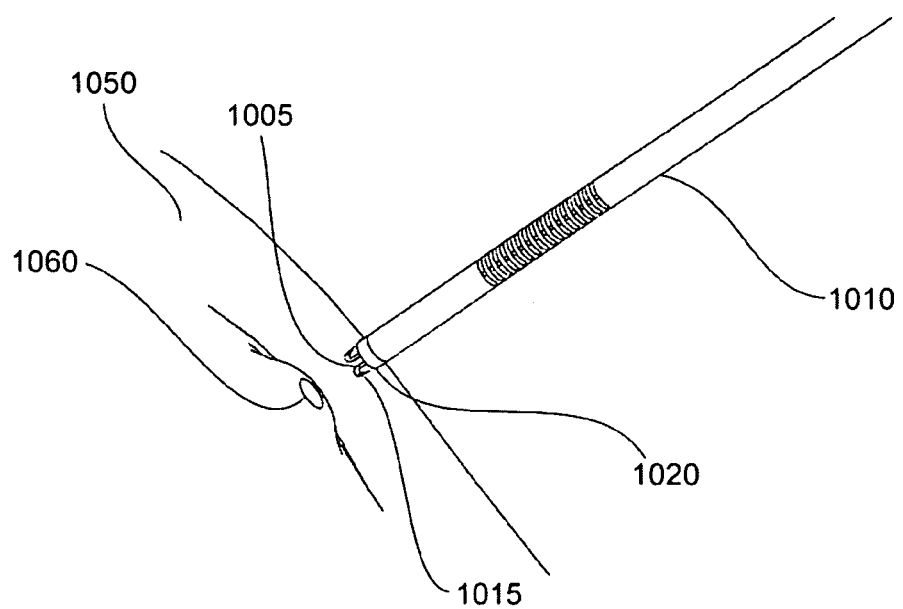
FIG. 10. Close up views of the distal end of a tissue approximation and fastening device according to another embodiment of the present invention, (A) pre-deployed, (B) inserted through hole in tissue, (C) moveable members deployed and tissue hooks positioned to engage distal tissue surface, (D) moveable members retracted and fastener assembly deployed.
Figure 10B:
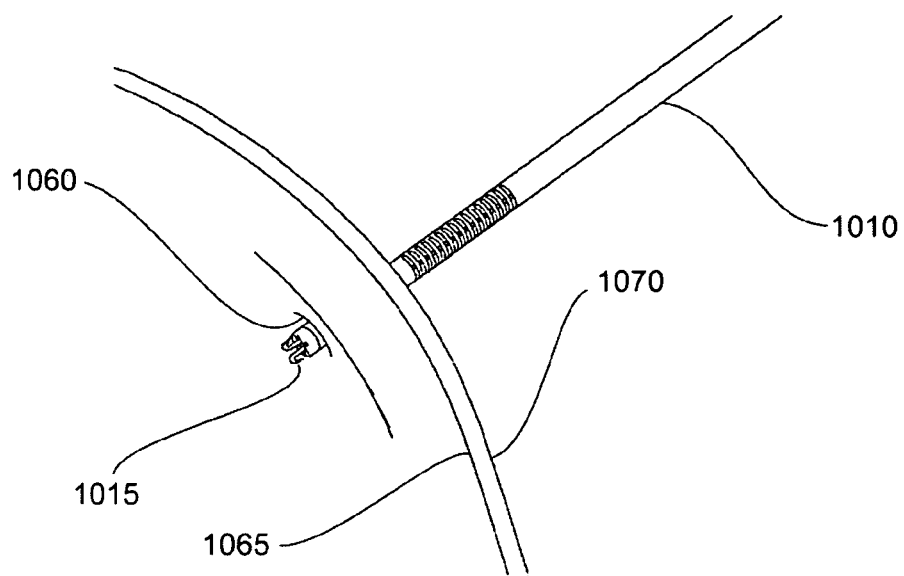

As shown in FIG. 10B, prior to actuating the tissue approximation function of the device, the distal end of longitudinal tube assembly 1010 is first passed at least part way into, and in some cases completely through, tissue layer 1050 via the opening in the tissue layer 1050 caused by hole-type defect 1060. As described previously, this example is similar to the situation a surgeon would encounter when finding it necessary to endoscopically close a hole though the gastrointestinal lumen created by the surgeon in order to access the abdominal cavity during a natural orifice transluminal endoscopic surgery (NOTES) procedure. By first passing the distal end of the device through the defect, this places the outward facing tissue hooks 1015 on the opposite side of the tissue layer from the direction of approach of the device, allowing the distal or exterior serosal tissue surface 1065 to be engaged and approximated rather than the proximal or interior mucosal tissue surface 1070.

Figure 10C:
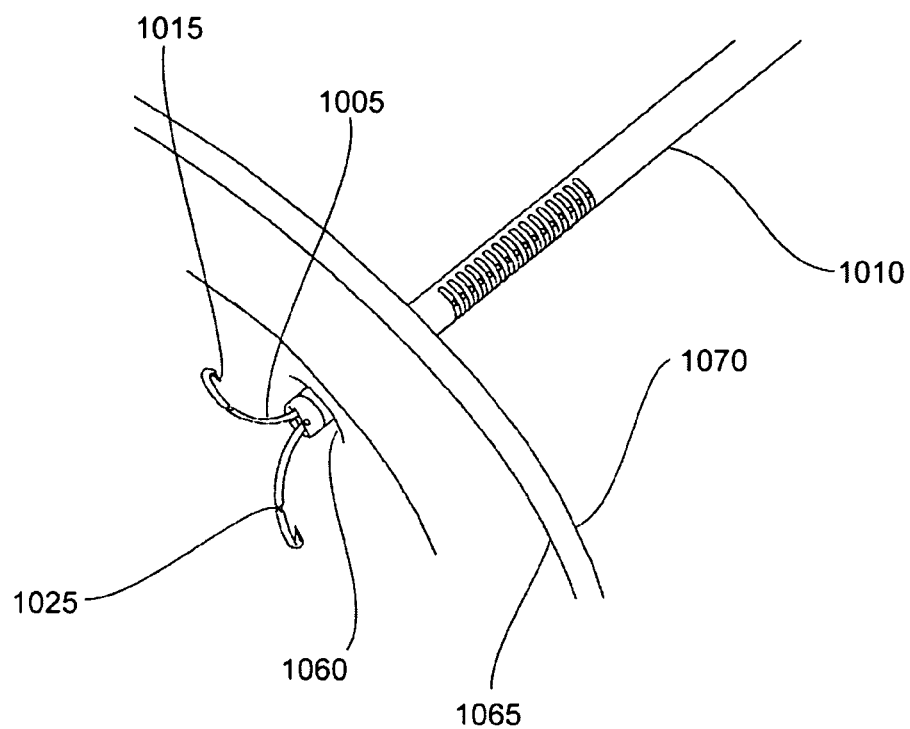

As seen in FIG. 10C, moveable arms 1005 are actuated and deployed by the user, positioning tissue hooks 1015 appropriately for engaging the tissue layer on its distal surface 1065 beyond the edges of the hole-type defect 1060. In this example (as well as the example of FIG. 8), where the goal is to close an access hole created through the gastrointestinal lumen during a NOTES procedure, the device may be inserted into the patient's gastrointestinal tract via a transoral or transanal endoscopic approach, and when passed through the defect and deployed, tissue hooks 1015 are positioned appropriately to engage the more robust and secure serosal tissue on the external surface of the gastrointestinal lumen. In this manner, when moveable arms 1005 are actuatingly retracted by the user, the engaged tissue on the distal surface of tissue layer 1050 is pulled proximally toward the distal end of the device, back through the tissue opening at defect 1060, effectively everting the tissue and bringing the exterior tissue surface into intimate contact with itself along the axis passing through the defect. In the case of the tissue layer being a gastrointestinal tissue layer, the external (extraluminal) tissue surface is covered with serosal tissue, which when brought into intimate contact as described above will heal by adhering to itself, producing a strong and durable serosa-to-serosa bond within 14 days after surgery, and thereby providing additional strength to the defect closure provided by system 1000, as described previously.

As further shown in FIG. 10C, moveable arms 1005 are configured having reduced cross section 1025 positioned proximally relative to tissue hooks 1015. The purpose of reduced cross section 1025 is to provide a pre-determined location where moveable arms 1005 will intentionally fracture when the tensile force generated within moveable arms 1005 during actuated retraction by the user (from within the proximal handle assembly, not shown) exceeds a designed value. Retainer ring 1020 is configured having surface features (not shown) on at least one internal surface of the openings through which moveable arms 1005 pass. Said surface features are designed to interact with opposing surface features (not shown) present on a slidably contacting surface of moveable arms 1005, distal to reduced cross section 1025. The interacting surface features on the inside of retainer ring 1025 and the distal portion of moveable arms 1005 are designed to be a one-way direction of travel mechanism. To describe this further, there is easy (low force requirement) sliding of moveable arms 1005 through the smooth slots in retainer ring 1020 when initially moving in the distal direction (i.e. during initial deployment of moveable arms 1005), but during the proximal motion of retraction, moveable arms 1005 are re-positioned (e.g. by a cam, latch, pivot or other similar mechanism, not shown) to slide inside non-smooth slots. In this manner, once moved proximally beyond a certain distance during retraction, a mechanism is engaged such that further distal motion is prevented and further proximal motion is incrementally controlled, similar to a ratchet. This mechanism is similar to the well known one-way direction of travel mechanisms used, for example, on plastic wire ties, which can be tightened by pulling in one direction, but cannot be loosened or removed by pulling in the opposite direction. Other mechanisms that achieve similar functional results are well known to those skilled in the art and may be used for the present purposes within the scope of the present invention, including various combinations of linear gears, levers, cams, springs and the like.

Figure 10D:
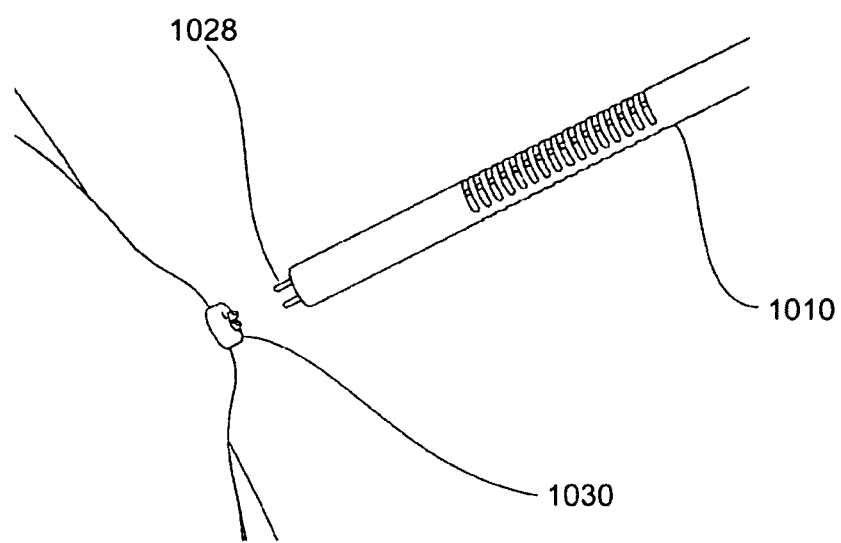

As illustrated in FIG. 10D, as moveable arms 1005 are retracted such that reduced cross section 1025 moves proximally of retainer ring 1020, the above described one-way direction of travel mechanism becomes actively engaged and causes a gradual compression and tightening of the tissue engaged by tissue hooks 1015 against the distal surface retainer ring 1020. Upon further retraction and tightening, the tensile forces within moveable arms 1005 are gradually increased until each of moveable arms 1005 fractures at the pre-determined positions defined by reduced cross section 1025. The fractured-off distal end of moveable arms 1005, including tissue hooks 1015 with tissue remaining engaged thereto, are then fixedly interconnected with retainer ring 1020, thereby becoming a unitary fastener assembly 1030. By actuating a mechanism in the proximal handle assembly (not shown) retainer ring 1020 is then releasably disengaged from pins 1028 positioned at the distal end of longitudinal tube assembly 1010, leaving fastener assembly 1030 implanted in the tissue as the securing means to hold the tissue in the approximated configuration, thereby closing hole-type defect 1060 in tissue layer 1050.

Figure 11:
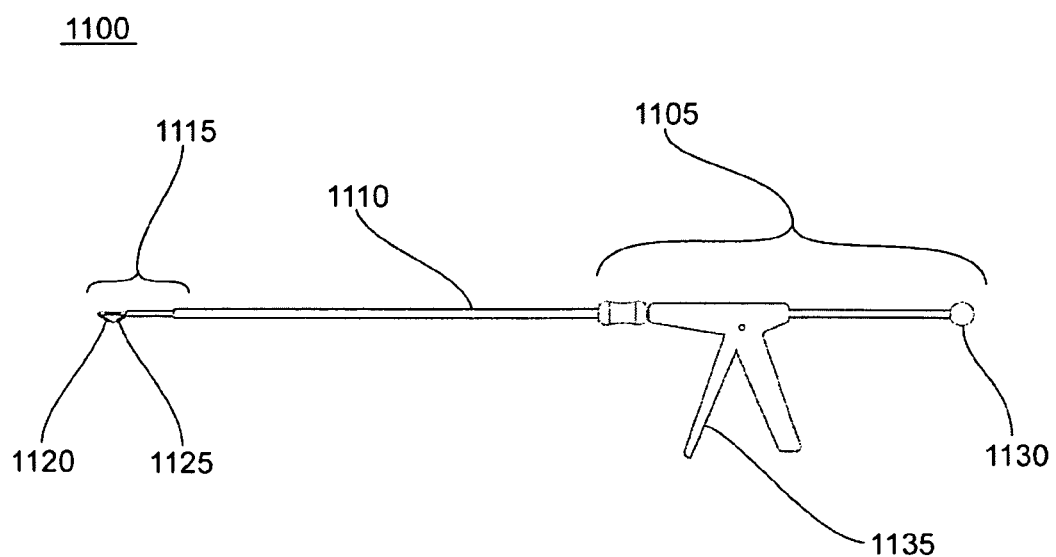
FIG. 11. Overview of an endoscopic system for tissue approximation and fastening according to another embodiment of the present invention.

Another embodiment of a tissue approximation and fastening system according to the present invention is shown in FIG. 11. System 1100 may be configured for use in laparoscopic, endoscopic or open procedures and consists of proximal handle assembly 1105, longitudinal tube assembly 1110 and distal tool assembly 1115. Distal tool assembly 1115, whose operation shall be explained in detail below, is shown in the pre-deployed configuration and includes distal tissue hook 1120 and proximal tissue hook 1125. Proximal tissue hook 1125 is releasably attached to the distal end of longitudinal tube assembly 1110, whereas distal tissue hook 1120 is positioned at the end of a moveable shaft 1122 (see below, FIG. 12) which is operably connected to proximal handle assembly 1105 via longitudinal tube assembly 1110. Proximal handle assembly is further configured having deployment knob 1130 and trigger 1135, whose functions will be described below.

FIG. 12 shows close up details of the distal end of system 1100, along with a target tissue layer 1250 in which the surgeon may be intending to create one or more tissue folds and secure said one or more folds to produce one or more plications, as may be desirable for example, in a procedure that reduces the volume of the gastrointestinal lumen as a surgical treatment for obesity. During initial actuated deployment, distal tissue hook 1120 is extended longitudinally and distally away from the end of the device when the user pushes deployment knob 1130 located on proximal handle assembly 1105. This causes distal tissue hook 1120 and proximal tissue hook 1125 to be spaced apart a user controlled distance and positioned appropriately for subsequent tissue engagement. The user is then able to engage tissue at each of two separately spaced apart locations by bringing the distal end of system 1100 into contact with target tissue layer 1250, where the distal longitudinal axis of the device 1205 is held substantially parallel to the surface of said tissue, as shown in FIG. 12A. While this particular embodiment is designed such that the distal longitudinal axis of the device 1205 must approach the tissue substantially parallel to its surface, as shown, it should be recognized that articulation and rotation mechanisms substantially similar to what was described previously (see device 100 and FIG. 5) can readily be incorporated into system 1100, if desired. In this manner, for example, the device may easily be used with conventional laparoscopic abdominal wall port placements and still allow the necessary parallel orientation relationship between the distal end of the device and the target tissue to be established for performing the tissue approximation and fastening.

It should be obvious to those skilled in the art that the user may optionally engage the two tissue locations simultaneously, or alternatively, either of the proximal tissue hook 1125 or distal tissue hook 1120 may be used to initially engage the tissue at a first location, followed by separate engaging of tissue at a second location using other tissue hook. Irrespective of the order of tissue engagement, fastener deployment proceeds as described below. The operational choice regarding the order of tissue engagement may therefore be made by the user, largely as a matter of convenience, based on the procedure, tissue type, patient's specific anatomy, etc.

Figure 12A:
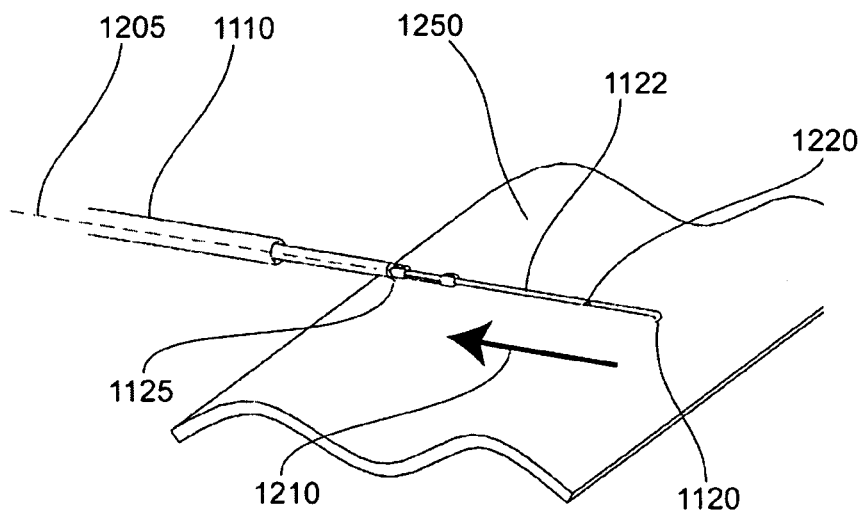
FIG. 12. Close up views of the distal end of an endoscopic system for tissue approximation and fastening according to another embodiment of the present invention (A) moveable members deployed and tissue engaged, (B) moveable arms being retracted to create a tissue fold, (C) tissue approximated and fastener assembly deployed, and (D) a plurality of fastener assemblies deployed producing a plication in the tissue.
Figure 12B:
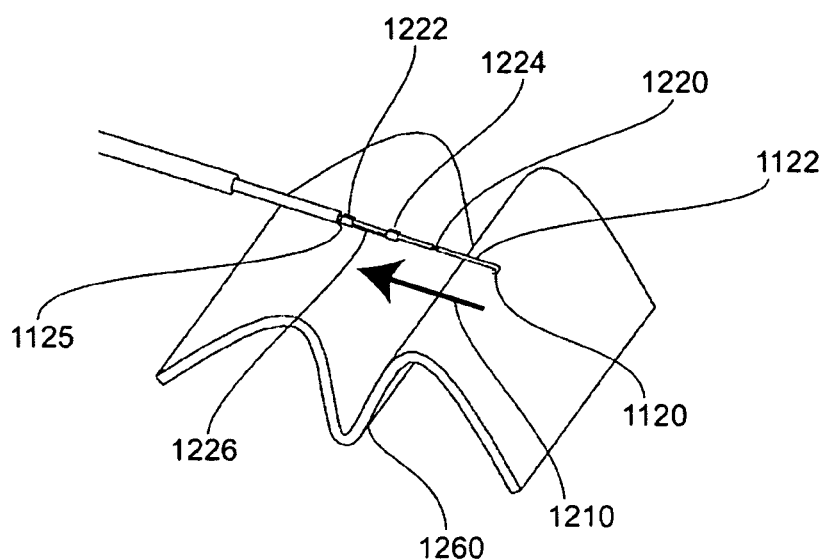

As further illustrated in FIG. 12A, once tissue has been engaged at each of the two separately spaced apart locations, the user actuates retraction of moveable shaft 1122 by squeezing trigger 1135 located on proximal handle assembly 1105. Trigger 1135 is operably connected to a suitable one-way ratchet-type mechanism (not shown) that is configured inside proximal handle assembly 1105. Said one-way ratchet-type mechanism is designed and configured to generate a tensile force 1210 that incrementally and forceably pulls moveable shaft 1122 in the proximal direction, while preventing its distal motion. Such mechanisms, similar to those used in caulking guns and the like, are very simple and well known in the art, typically being constructed using a linear gear and one or more levers, cams, springs, and the like. The continued actuated retraction of moveable shaft 1122 by the operator draws distal tissue hook 1120, with the tissue engaged thereto, toward proximal tissue hook 1125, causing the engaged tissue locations to be approximated near the distal end of the device. In one exemplary usage of this device, a fold 1260 may be created in the tissue, as shown in FIG. 12B. To improve safety and provide the surgeon flexibility to ensure the tissue approximation is proceeding in the desired manner, before delivering the fastening means, system 1100 may optionally be configured with a release mechanism (not shown) that allows the user to quickly and easily disengage the one-way ratchet mechanism, thereby releasing moveable shaft and allowing it to again be moved distally. In this manner the surgeon may disengage from tissue or reposition the device before re-initiating tissue approximation.

In terms of deploying a fastener assembly to securely hold the tissue in the approximated configuration, distal tool assembly 1115 of system 1100 is constructed and operates in a substantially similar manner to that described previously for system 1000 (FIG. 10). Accordingly, shown in FIG. 12A and FIG. 12B is reduced cross section 1220 on moveable shaft 1122, located at a pre-determined position proximal to distal tissue hook 1120. The purpose of reduced cross section 1220 is to provide a specified location where moveable shaft 1122 will intentionally fracture when the tensile force generated within moveable shaft 1122 during actuated retraction by the user exceeds a designed value.

In this embodiment, the pre-deployed fastener assembly is initially fixedly interconnected with proximal tissue hook 1125 (which is releasably attached to the distal end of longitudinal tube assembly 1110), consisting of proximal guide 1222, distal guide 1224 and rail 1226 positioned therebetween. Moveable shaft 1122 slides inside the proximal and distal guides such that there is created a sliding contact interface between rail 1226 and moveable shaft 1122. Interacting surface features (e.g. directional teeth, ridges, bumps, etc.) are present on the inside contact surface of rail 1226, and also on the inside contact surface of moveable shaft 1122 in between proximal tissue hook 1125 and reduced cross section 1220. These interacting surface features are designed to provide a one-way direction of travel mechanism, similar to that used in plastic wire ties, well known in the art, and previously described previously in FIG. 10 with regard to system 1000. In this manner, when the user actuates retraction of sliding shaft 1122 using trigger 1135, after the reduced cross section of moveable shaft 1122 moves proximally beyond distal guide 1224, the one-way direction of travel mechanism becomes actively engaged, resulting in a mating of the fastener assembly components (i.e. proximal tissue hook 1125, proximal guide 1222, distal guide 1224, rail 1226, and the broken off portion of moveable shaft 1122 with distal tissue hook 1120 attached thereto). Further actuated retraction by the user results in approximation of the engaged tissue locations and gradual compressive tightening as distal tissue hook 1120 and proximal tissue hook 1125 are ratcheted toward one another.

Figure 12C:
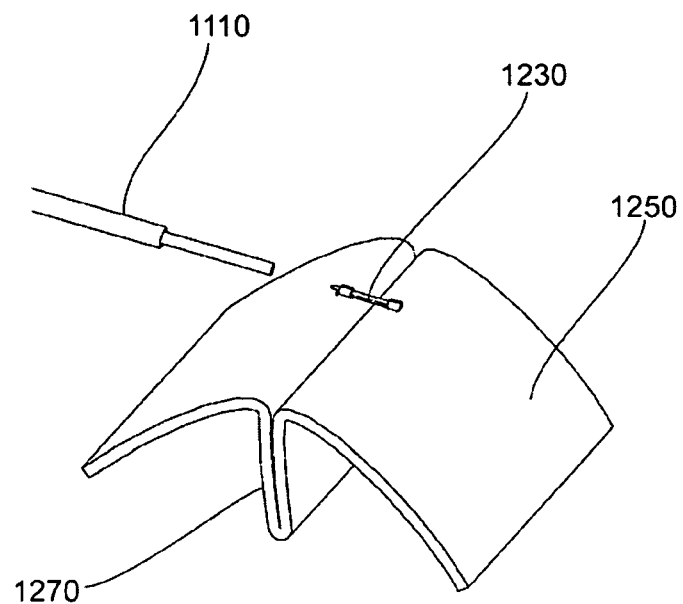

Continued retraction by the user gradually increases the tensile force within moveable shaft 1122 until reduced cross section 1220 fractures at the designed force value. As shown in FIG. 12C, proximal tissue hook 1125 is then releasably disengaged from the distal end of longitudinal tube assembly 1110 leaving the deployed unitary fastener assembly 1230 implanted in the tissue as the securing means to hold the tissue in the approximated configuration, in this example producing plication 1270 within target tissue layer 1250.

Figure 12D:
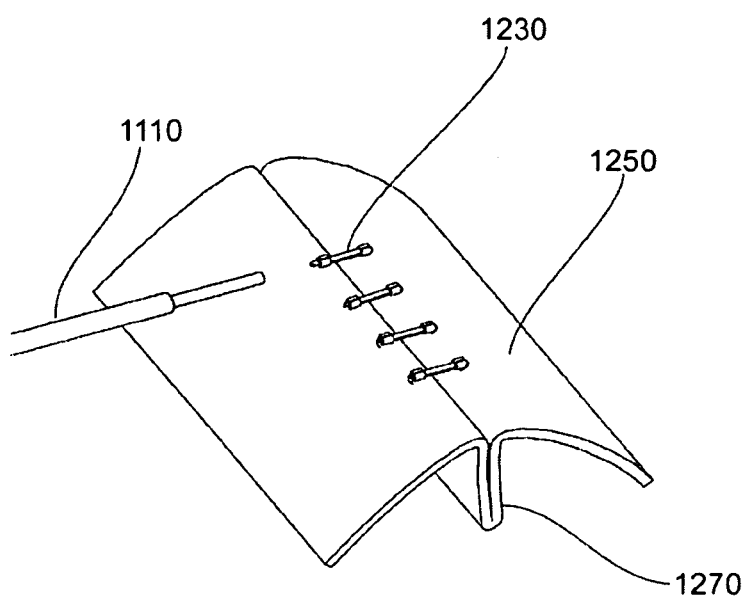

System 1100 as illustrated is a single loading unit device, designed to approximate tissue and deploy a single fastener assembly as described above. Accordingly, this device may be withdrawn from the patient, reloaded, then re-inserted and positioned appropriately to allow the surgeon to repeat the aforementioned operational steps any number of times, thereby extending the tissue approximation and fastening capabilities beyond a single firing. This may be useful, for example, in order to produce a longer and more securely fastened plication, as illustrated in FIG. 12D. While the embodiment of system 1100 shown in FIG. 11 and FIG. 12 is a single loading unit device, various engineering design and construction modifications may be made using methods well known in the art in order to produce multi-fire device embodiments operating on substantially similar design principles; such embodiments are considered obvious extensions of the novel technology described herein and are therefore considered within the scope of the present invention.

In certain other embodiments of the present invention, it is possible to configure the devices such that the distal tool assembly provides a multi-functional mechanism that is designed to both approximate and fasten tissue. This can potentially further reduce the complexity and cost of the device. For example, in contrast to the distal tool assembly described in FIG. 7, which provides separate actuatingly operable mechanisms for approximating and fastening the tissue, the alternative embodiment described below uses a partially deployed fastener to serve as the extendable members of the present invention that are used to engage tissue. In this embodiment, with the fastener positioned in the partially deployed configuration, according to the methods of the present invention, tissue may be engaged at one location, the device may then be repositioned to engaged tissue at a second location, moving the first engaged tissue location toward the second engaged tissue location in order to approximate the tissues near the distal end of the device, and then the fastener may be fully deployed and released from the device to secure the tissue in the approximated configuration.

Figure 13:
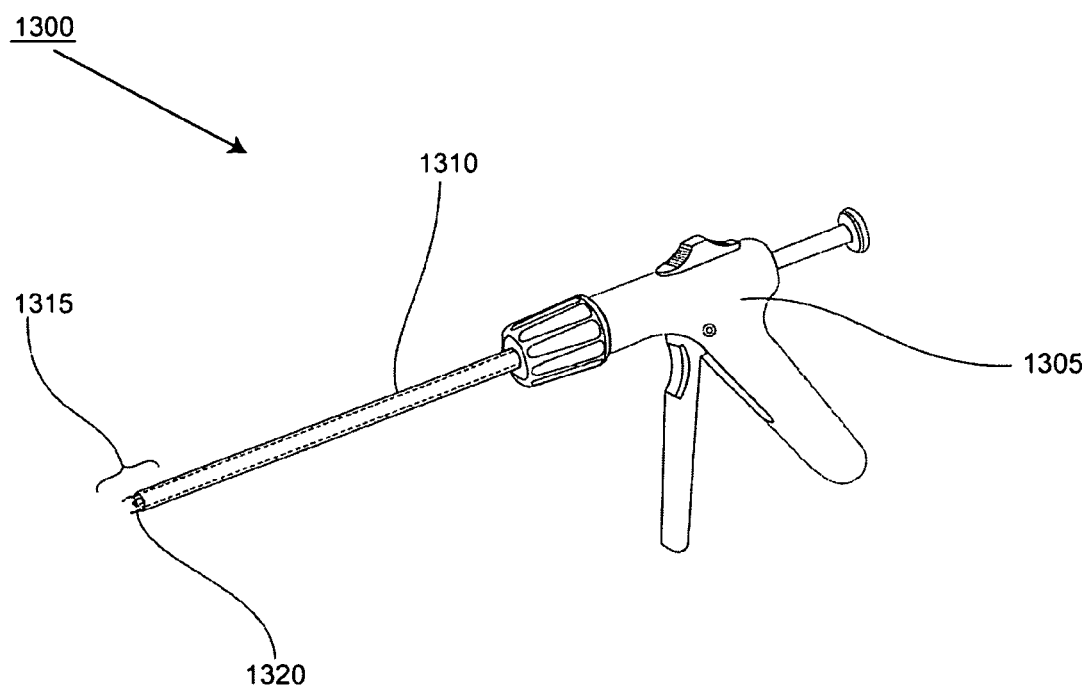
FIG. 13. Overview of a system for tissue approximation and fastening according to another embodiment of the present invention.

One such embodiment is illustrated in FIG. 13, which shows an overview of a laparoscopic device 1300 having handle assembly 1305, longitudinal tube assembly 1310 and distal tool assembly 1315. Distal tool assembly 1315 is configured having at least one tissue engaging fastener 1320 that is capable of being releasably held in a partially-deployed configuration, during which time it is used to carry out the tissue approximation functions of the device. In the partially-deployed configuration at least one or more tissue penetrating members of fastener 1320 that are capable of engaging tissue are sufficiently exposed beyond the distal end of the device so as to allow tissue to be engaged at two or more locations. Further details of this device configuration and its use to approximate and fasten tissue will be described below.

Figure 14A:
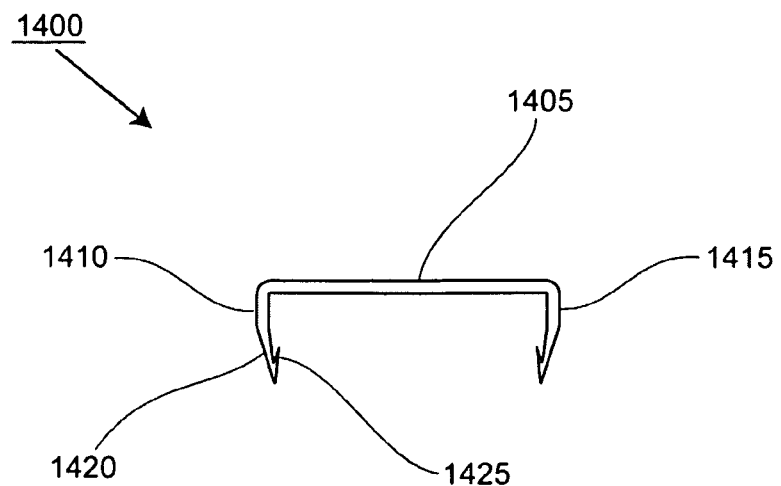
FIG. 14. A fastener for use in conjunction with a system for tissue approximation and fastening according to another embodiment of the present invention (A) pre-deployed configuration, and (B) deployed configuration.
Figure 14B:
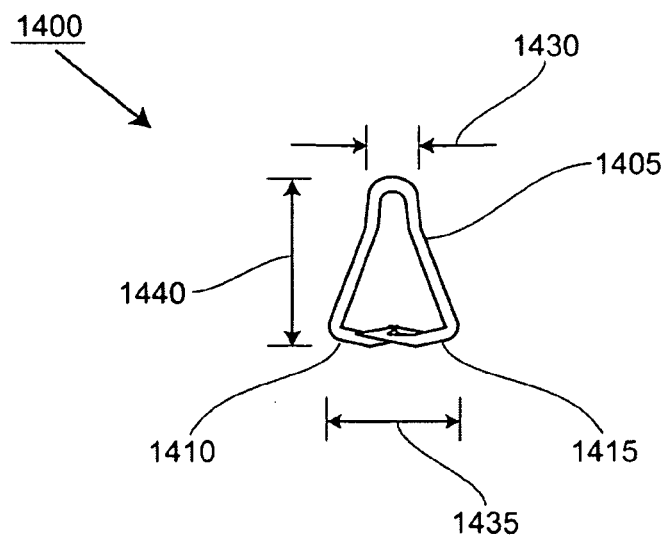

An exemplary tissue fastener of the present invention is a deformable box-type staple 1400 shown in the pre-deployed configuration in FIG. 14A and in the deployed configuration in FIG. 14B. This type of fastener is compatible with various embodiments of the present invention, such as the embodiments described in FIG. 7 and/or FIG. 13. In the pre-deployed configuration, box-type staple 1400 consists of deformable proximal member 1405 and two or more tissue penetrating members, such as tissue penetrating members 1410 and 1415. Each tissue penetrating member is further configured having a tissue engagement mechanism configured in proximity to its distal end. In the example shown, the tissue engagement mechanism consists of sharpened tip 1420 combined with inward pointing barb 1425. Sharpened tip 1420 promotes penetration of tissue with a low force requirement, whereas after tissue engagement, inward pointing barb 1425 prevents the tissue from accidentally slipping or disengaging from the tissue penetrating member during subsequent tissue manipulation. During fastener deployment, after tissue has been approximated by the device, proximal member 1405 is deformably reconfigured by the distal tool assembly (e.g. by operator actuation of the handle assembly, not shown) such that tissue penetrating members 1410 and 1415 first move toward and then slide past one another. In the final deployed configuration tissue penetrating members 1410 and 1415 overlap, as shown in FIG. 14B, such that box-type staple 1400 assumes a continuous, closed loop profile wherein no sharpened tips are exposed that may result in accidental tissue damage or chronic irritation by the implant. Deployed box-type staple 1400 is preferably reconfigured into an unique shape, such as, for example, the polygonal shape illustrated in FIG. 14B. In this example, the smallest dimension in staple width 1430 occurs near its proximal end, at the position along the deformable proximal member where the fastener was releasably held by device 1300 in its pre-deployed and/or partially deployed configuration. In contrast, the largest dimension in staple width 1435 occurs at the distal end near where tissue penetrating members 1410 and 1415 overlap. Note also that in the deployed configuration, box-type staple 1400 has an overall length dimension (i.e. the distance dimension along the longitudinal axis of the device) 1440 that exceeds its maximum width dimension 1435, meaning the staple aspect ratio is configured such that it is relatively longer along a direction parallel to the longitudinal axis of the device. This exemplary staple shape and aspect ratio is notably different from prior art box-type staples, and is considered a unique feature of one fastener embodiment of the present invention. While not obvious, it has been found through experimentation that this polygonal deployed shape of box-type staple represents an optimal tradeoff between several competing needs. For example, it is desirable to provide sufficiently long tissue penetrating members to promote positive tissue engagement while in the pre-deployed and/or partially deployed configuration. At the same time, it is also desirable to provide a high degree of compression to the tissue enclosed within the staple and to minimize the widest staple dimension 1435 so as to prevent the tissues inside the staple from pulling very far apart under tension. It is yet further desirable to avoid exposure of sharp tips in the final deployed configuration. Note that, due to the orientation of the plane defining the interfacial contact area between the two approximated tissue surfaces relative to the orientation of the staple during deployment, in the deployed configuration this unique staple shape and aspect ratio provides for direct compression across a larger interfacial contact area than is possible with prior art box-type staples having a B-shape, D-shape, etc. These are significant advantages of this unique polygonal-shaped deployed box-type staple when used in conjunction with the tissue approximation and fastening devices of the present invention.

Figure 15:
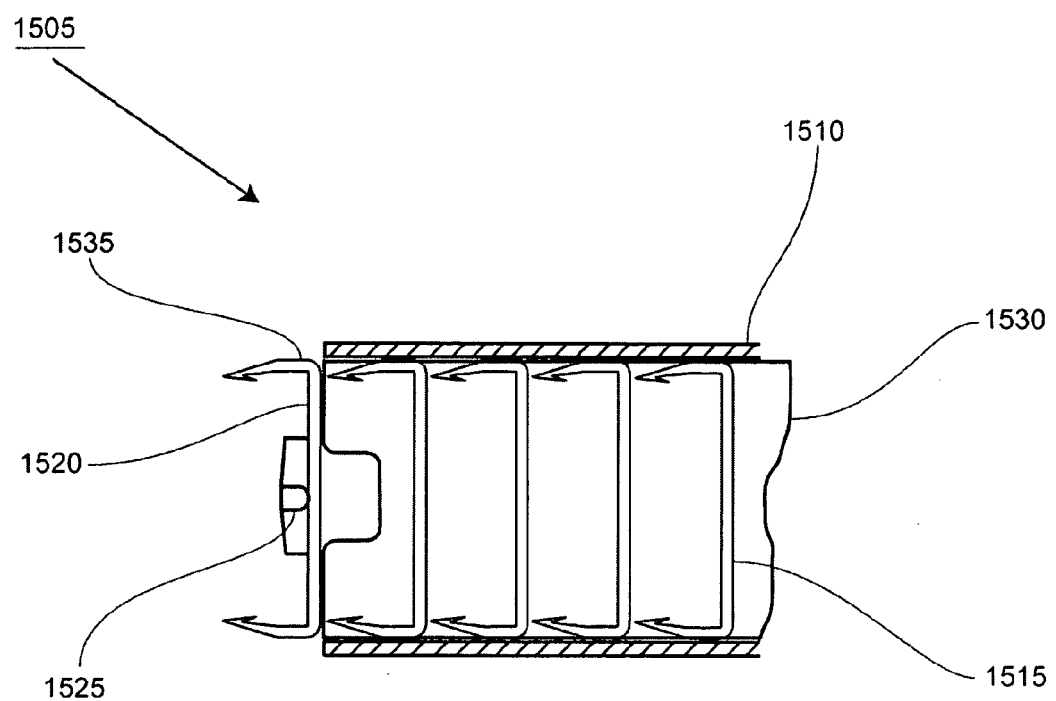
FIG. 15. Close up view of the distal end of an system for tissue approximation and fastening according to another embodiment of the present invention.
Figure 16A:
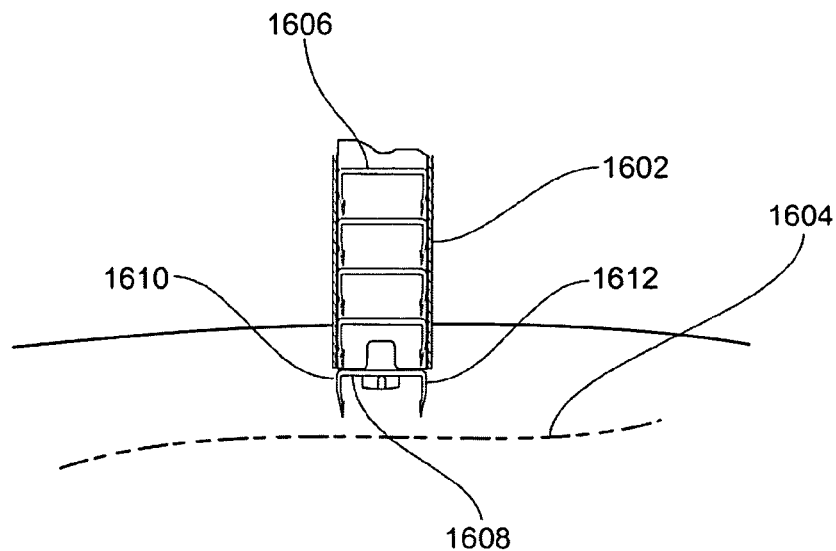
FIG. 16. Close up views of the distal end of a system for tissue approximation and fastening showing a method of use according to one embodiment of the present invention (A) device positioned above tissue surface, (B) tissue engaged at a first location, (C) device repositioned to engaged tissue at a second location, (D) two engaged tissue locations approximated near the distal end of the device to create an invaginated tissue fold, and (E) box-type staple deployed to secure tissue in the approximated configuration.
Figure 16B:
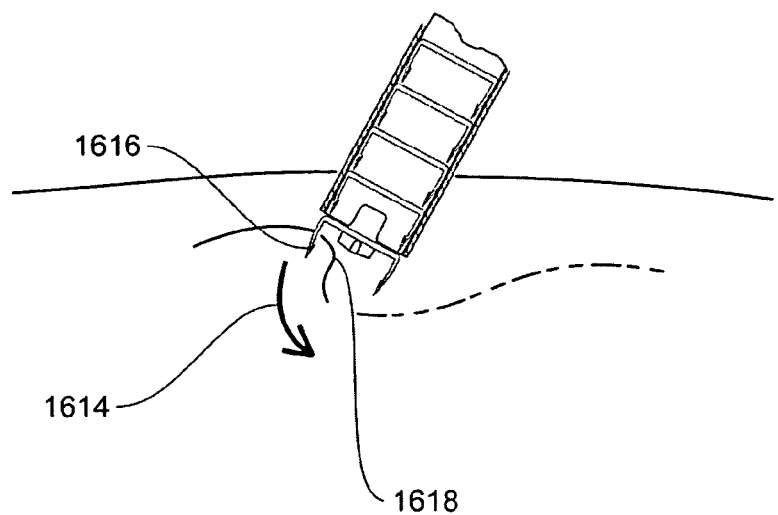
Figure 16C:
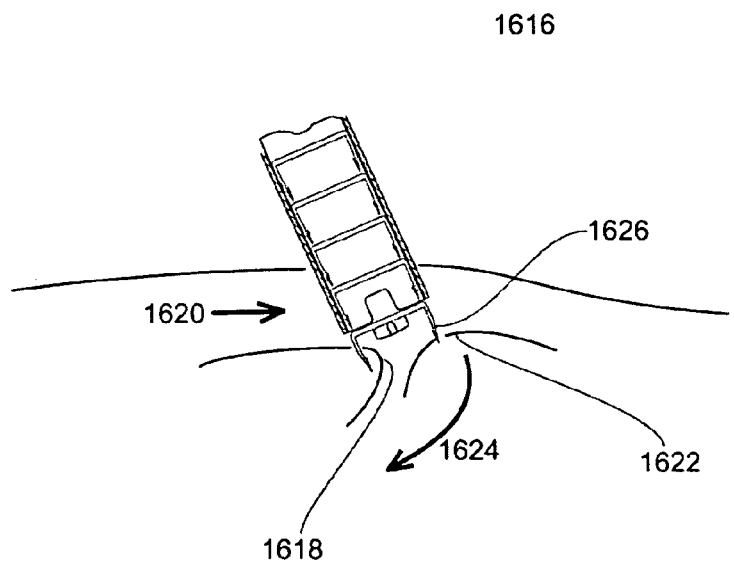
Figure 16D:
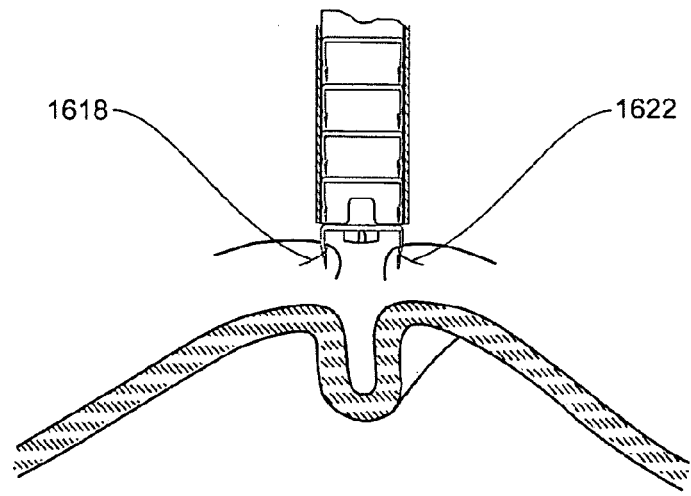
Figure 16E:
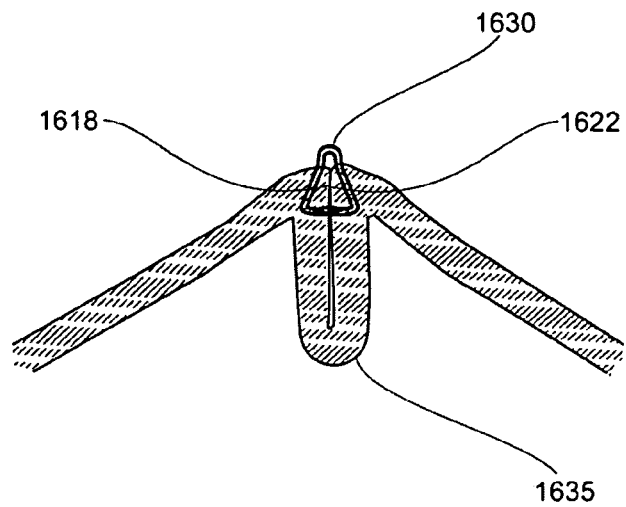

Referring again to FIG. 13, and assuming an exemplary fastener such as that illustrated in FIG. 14 is utilized, FIG. 15 shows a close-up view of the distal end of a device according to one embodiment of the present invention. In this example, distal tool assembly 1505 is configured at the distal end of a longitudinal tube assembly. One or more fasteners may be initially provided in a pre-deployed configuration, such as pre-deployed box-type staples 1515, that are slidably held, temporarily stored or otherwise moveably positioned within outer tube assembly 1510. Upon initial actuation by the operator (e.g. remotely from the handle assembly, not shown) the fastener may be moved (e.g. by a spring loaded mechanism) from its initial pre-deployed configuration to a partially deployed configuration, such as partially deployed box-type staple 1520. In the partially deployed configuration, box-type staple 1520 is held firmly, yet releasably in place by frictional forces between stationary anvil 1525 and movable staple former 1530. In some configurations (not shown) it may be desirable to incorporate one or more features such as notches, grooves, indentations, or the like, into the deformable proximal member of box-type staple 1520 to prevent slippage or inadvertent premature release of the staple while held in the partially deployed configuration. Moveable staple former 1530 may be configured in operable communication with various springs, gears, ratchets or other similar mechanisms known in the art for reversing its direction of travel during staple advancement and for transmitting an appropriate linear mechanical force needed to hold the staple securely against stationary anvil 1525. Note in the partially deployed configuration the tissue penetrating members 1535 are exposed beyond the distal end of the device. In this manner, exposed tissue penetrating members 1535, having distal tissue engagement mechanisms attached thereto (as described in FIG. 14), may be used for engaging and approximating tissue, as described in FIG. 16 below. An advantage of this device configuration is that, beyond the staple actuation mechanisms, no additional members, moveable components, mechanisms, etc. are needed to engage and approximate tissue. After tissue approximation, the operator actuates the device, moving staple former 1530 distally relative to stationary anvil 1525. This deforms the box-type staple, reconfiguring it into its fully deployed polygonal shape and thereby compresses the tissues enclosed between tissue penetrating members. Finally, the fully deployed box-type staple is released from the distal end of the device and left behind implanted in the tissue to secure the tissue in the approximated configuration. Note that during actuated staple forming it is the dimensions and shapes of the mating surfaces, as well as the applied forces between stationary anvil 1525 and moveable staple former 1530 that may be optimized to control the final deployed polygonal staple configuration, preferably as described in FIG. 14.

According to the embodiments described above in FIG. 13-FIG. 15, during use, the sequence of steps for approximating and fastening tissue for the exemplary purpose of creating an invaginated tissue fold is illustrated in FIG. 16. As shown in FIG. 16A, after insertion of the device into the patient's body distal tool assembly 1602 is first positioned above and in proximity to the target tissue surface 1604. The device is then actuated and a box-type staple is moved from its initial pre-deployed configuration 1606 to the partially deployed configuration 1608, in which tissue penetrating members 1610 and 1612 are moved into an exposed position. As shown in FIG. 16B, the position of the device may then be manipulated by the operator (e.g. by any combination of motions such as pushing, pulling, rotating, dragging, pivoting, and the like, as shown at 1614) to allow a first tissue engagement mechanism 1616, configured as part of a first tissue penetrating member 1610, to engage tissue at a first target location 1618 on the tissue surface. As shown in FIG. 16C, the distal end of the device, having the first target tissue 1618 attached thereto, is then moved as shown at 1620, and repositioned to be in proximity to a second target tissue location 1622 on the tissue surface. The device is then again manipulated by the operator as shown at 1624 in order to allow a second tissue engagement mechanism 1626, configured as part of second tissue penetrating member 1612, to engage tissue at the second target location 1622 on the tissue surface. In this manner, tissue has been operatively engaged at two separately spaced locations 1618 and 1622 on the tissue surface and the engaged tissues have been moved toward one another and approximated near the distal end of the device, as illustrated in FIG. 16D. After the operator again actuates the device, as shown in FIG. 16E, the box-type staple is deformably reconfigured from its partially deployed configuration 1608 to its fully deployed configuration 1630, after which it is released from the device and left implanted in the tissue to securely hold the tissue in the approximated configuration. In the example shown, as a result of using the devices of the present invention according to the methods of the present invention in order to approximate and fasten tissue, an invaginated tissue fold 1635 has been produced. Tissue fold 1635 projects away from the distal end of the device and the tissue engagement locations 1618 and 1622 are held in substantially intimate contact inside the tissue fold.

We claim:

1. A method for approximating and fastening tissue comprising sequentially: positioning a device having a distal tool assembly incorporating at least one tissue fastener having two or more tissue penetrating members in a pre-deployed configuration in proximity to target tissue surface; moving the at least one tissue fastener from its pre-deployed position within the distal tool assembly to a partially deployed configuration in which at least two tissue penetrating members of the tissue fastener are exposed beyond the distal end of the device; engaging tissue at a first location with at least one penetrating member of the at least one tissue fastener; repositioning the engaged tissue and the at least one tissue penetrating member to approximate tissue at the first location toward a second location and forming an invaginated tissue fold projecting away from the distal tool assembly and the first and second location; engaging tissue at the second location with another of the tissue penetrating members; and deformably reconfiguring the tissue fastener from its partially deployed configuration to its fully deployed configuration and releasing the tissue fastener from the tool assembly to securely hold the first and second tissue locations in the approximated configuration, thereby securing the invaginated tissue fold.

2. The method of claim 1, wherein the tissue penetrating members have barbs.

3. The method of claim 1, wherein the at least one tissue fastener is a staple and wherein deformably reconfiguring the at least one staple reconfigures the staple such that the tissue penetrating members move toward and then move past one another.

4. The method of claim 1, wherein deformably reconfiguring the at least one tissue fastener deformably reconfigures the tissue fastener in a polygonal-shaped loop.

5. The method of claim 1, wherein deformably reconfiguring the at least one tissue fastener deformably reconfigures the tissue fastener such that a smallest deployed dimension of the tissue fastener occurs near its proximal end and a largest deployed dimension occurs at a distal end near where tissue penetrating members overlap.

6. The method of claim 1, wherein deformably reconfiguring the at least one tissue fastener deformably reconfigures the tissue fastener such that a overall length dimension in the direction of tissue penetration exceeds a maximum width dimension.

7. The method of claim 1, wherein tissue is engaged at first and second spaced apart tissue engagement locations sequentially.

8. The method of claim 1, additionally comprising performing successive tissue engagement, approximation and securing steps.

9. The method of claim 1, performed without removing the device from its position in proximity to the tissue surface.

10. method of claim 1, wherein repositioning the engaged tissue to approximate the first and second target tissue locations is achieved by an operator dragging the first engaged tissue location to the second location, thereby approximating the engaged tissue locations.

11. The method of claim 1, wherein the two or more tissue penetrating members are configured as opposing legs of a deformable staple.

12. The method of claim 1, wherein the tissue penetrating members have sharpened tips.

13. The method of claim 1, wherein engaging tissue at the first location is achieved by manipulating the position of the distal tool assembly.

14. The method of claim 1, wherein repositioning engaged tissue is achieved by manipulating the position of the distal tool assembly using pushing, pulling, rotating, dragging or pivoting motions.

15. The method of claim 1, wherein the tissue fastener is a box-type staple.

16. The method of claim 1, wherein the at least one tissue fastener is a deformable staple and the tissue penetrating members are opposing legs of the deformable staple.

17. The method of claim 1, wherein the first and second tissue engagement locations are spaced apart further than the distance between the tissue penetrating members.

* * * * *